United States Patent
Christiansen et al.

(10) Patent No.: US 9,206,105 B2
(45) Date of Patent: Dec. 8, 2015

(54) MIXTURE OF BISPHOSPHITES AND USE THEREOF AS A CATALYST MIXTURE IN HYDROFORMYLATION

(71) Applicants: Andrea Christiansen, Rostock (DE); Robert Franke, Marl (DE); Dirk Fridag, Haltern am See (DE); Dieter Hess, Marl (DE); Katrin Marie Dyballa, Recklinghausen (DE); Bernd Hannebauer, Muehlheim (DE)

(72) Inventors: Andrea Christiansen, Rostock (DE); Robert Franke, Marl (DE); Dirk Fridag, Haltern am See (DE); Dieter Hess, Marl (DE); Katrin Marie Dyballa, Recklinghausen (DE); Bernd Hannebauer, Muehlheim (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/434,879

(22) PCT Filed: Sep. 27, 2013

(86) PCT No.: PCT/EP2013/070226
§ 371 (c)(1),
(2) Date: Apr. 10, 2015

(87) PCT Pub. No.: WO2014/056736
PCT Pub. Date: Apr. 17, 2014

(65) Prior Publication Data
US 2015/0274627 A1 Oct. 1, 2015

(30) Foreign Application Priority Data

Oct. 12, 2012 (DE) .......................... 10 2012 218 625
Oct. 12, 2012 (DE) .......................... 10 2012 218 627
Oct. 12, 2012 (DE) .......................... 10 2012 218 629
Oct. 12, 2012 (DE) .......................... 10 2012 218 630

(51) Int. Cl.
*C07C 45/50* (2006.01)
*B01J 31/18* (2006.01)
*B01J 31/02* (2006.01)
*C07F 9/6568* (2006.01)

(52) U.S. Cl.
CPC ........... *C07C 45/505* (2013.01); *B01J 31/0237* (2013.01); *B01J 31/0271* (2013.01); *B01J 31/185* (2013.01); *B01J 2231/321* (2013.01); *B01J 2531/822* (2013.01); *C07F 9/65683* (2013.01); *C07F 9/65685* (2013.01)

(58) Field of Classification Search
CPC ..................... C07F 9/65683; C07F 9/65685
USPC .......................................................... 568/12
See application file for complete search history.

(56) References Cited

U.S. PATENT DOCUMENTS

| 4,067,890 | A |   | 1/1978  | Rutledge |
|-----------|---|---|---------|----------|
| 4,668,651 | A | * | 5/1987  | Billig et al. .................. 502/158 |
| 4,769,498 | A |   | 9/1988  | Billig et al. |
| 5,202,297 | A |   | 4/1993  | Lorz et al. |
| 5,288,918 | A |   | 2/1994  | Maher et al. |
| 5,312,996 | A |   | 5/1994  | Packett |
| 5,981,772 | A | * | 11/1999 | Foo et al. ...................... 549/349 |
| 6,120,700 | A | * | 9/2000  | Foo et al. ................... 252/182.3 |
| 8,461,394 | B2 |  | 6/2013  | Lueken et al. |
| 8,884,070 | B2 |  | 11/2014 | Franke et al. |
| 2003/0195368 | A1 | | 10/2003 | Rottger et al. |
| 2011/0130595 | A1 | | 6/2011 | Lueken et al. |
| 2015/0018576 | A1 | | 1/2015 | Baumgarten et al. |

FOREIGN PATENT DOCUMENTS

| DE | 25 36 870 A1      | 3/1976  |
| DE | 10 2008 002 187 A1 | 12/2009 |
| EP | 1 294 731 B1      | 2/2004  |
| EP | 2 003 138 A1      | 12/2008 |
| WO | WO 95/28228 A1    | 10/1995 |
| WO | WO 2014/056735 A1 | 4/2014  |
| WO | WO 2014/056737 A1 | 4/2014  |

OTHER PUBLICATIONS

U.S. Appl. No. 14/434,988, filed Apr. 10, 2015, Christiansen, et al.
U.S. Appl. No. 14/434,827, filed Apr. 10, 2015, Christiansen, et al.
U.S. Appl. No. 14/435,007, filed Apr. 10, 2015, Christiansen, et al.
U.S. Appl. No. 14/435,052, filed Apr. 10, 2015, Fridag, et al.
International Search Report issued Jan. 7, 2014 in PCT/EP2013/070226.
Office Action issued Jun. 25, 2013 in German Patent Application No. 10 2012 218 625.5.
Office Action issued Jun. 25, 2013 in German Patent Application No. 10 2012 218 627.1.
Office Action issued May 31, 2013 in German Patent Application No. 10 2012 218 629.8.
Office Action issued May 31, 2013 in German Patent Application No. 10 2012 218 630.1.

* cited by examiner

*Primary Examiner* — Elvis O Price
(74) *Attorney, Agent, or Firm* — Oblon, McClelland, Maier & Neustadt, L.L.P.

(57) ABSTRACT

The invention relates to a mixture of bisphosphites, to a process for preparation thereof, and to the reaction thereof with metals to give mixtures comprising complexes of the constitutionally isomeric bisphosphites and the metal, and to the use thereof as a catalytically active composition in hydroformylation reactions, and also to the hydroformylation reaction itself.

19 Claims, 3 Drawing Sheets

○ C    ○ H

MIXTURE OF BISPHOSPHITES AND USE THEREOF AS A CATALYST MIXTURE IN HYDROFORMYLATION

The invention relates to a mixture of bisphosphites, to a process for preparation thereof, and to the reaction thereof with metals to give mixtures comprising complexes of the constitutionally isomeric bisphosphites and the metal, and to the use thereof as a catalytically active composition in hydroformylation reactions, and also to the hydroformylation reaction itself.

The reactions between olefin compounds, carbon monoxide and hydrogen in the presence of a catalyst to give the aldehydes with one carbon atom more is known as hydroformylation or the oxo process. The catalysts used in these reactions are frequently compounds of the transition metals of group VIII of the Periodic Table of the Elements. Known ligands are, for example, compounds from the classes of the phosphines, phosphites and phosphonites, each with trivalent phosphorus $P^{III}$. A good overview of the state of the hydroformylation of olefins can be found in B. CORNILS, W. A. HERRMANN, "Applied Homogeneous Catalysis with Organometallic Compounds", vol. 1 & 2, VCH, Weinheim, New York, 1996 or R. Franke, D. Selent, A. Börner, "Applied Hydroformylation", Chem. Rev., 2012, DOI:10.1021/cr3001803.

Every catalytically active composition has its specific benefits. According to the feedstock and target product, therefore, different catalytically active compositions are used.

U.S. Pat. No. 4,694,109 and U.S. Pat. No. 4,879,416 describe bisphosphine ligands and use thereof in the hydroformylation of olefins at low synthesis gas pressures. Particularly in the case of hydroformylation of propene, ligands of this type achieve high activities and high n/i selectivities (n/i=the ratio of linear aldehyde (=n) to branched (=iso) aldehyde). WO 95/30680 discloses bidentate phosphine ligands and the use thereof in catalysis, including in hydroformylation reactions. Ferrocene-bridged bisphosphines are described, for example, in patent specifications U.S. Pat. No. 4,169,861, U.S. Pat. No. 4,201,714 and U.S. Pat. No. 4,193,943 as ligands for hydroformylations.

The disadvantage of bi- and polydentate phosphine ligands is a relatively high level of complexity necessary for preparation thereof. It is therefore often unfeasible to use such systems in industrial operations. An additional factor is comparatively low activity, which has to be compensated for by chemical engineering, through high residence times. This in turn leads to unwanted side reactions of the products.

Rhodium monophosphite complexes in catalytically active compositions are suitable for the hydroformylation of branched olefins having internal double bonds, but the selectivity for terminally hydroformylated compounds is low. EP 0 155 508 discloses the use of bisarylene-substituted monophosphites in the rhodium-catalysed hydroformylation of sterically hindered olefins, e.g. isobutene.

Catalytically active compositions based on rhodium-bisphosphite complexes are suitable for the hydroformylation of linear olefins having terminal and internal double bonds, forming predominantly terminally hydroformylated products. In contrast, branched olefins having internal double bonds are converted only to a small degree. When they coordinate to a transition metal site, these phosphites give rise to catalysts of enhanced activity, but the service life characteristics of these catalytically active compositions is unsatisfactory, one reason being the hydrolysis sensitivity of the phosphite ligands. The use of substituted bisaryldiols as starting materials for the phosphite ligands, as described in EP 0 214 622 or EP 0 472 071, achieved considerable improvements.

According to the literature, the catalytically active compositions of these ligands based on rhodium are exceptionally active in the hydroformylation of α-olefins. U.S. Pat. No. 4,668,651, U.S. Pat. No. 4,748,261 and U.S. Pat. No. 4,885,401 describe polyphosphite ligands with which α-olefins, but also 2-butene, can be converted with high n/i selectivity to the terminally hydroformylated products. Bidentate ligands of this type were also used for hydroformylation of butadiene (U.S. Pat. No. 5,312,996).

The bisphosphites disclosed in EP 1 294 731 have olefin conversions up to 98% in the hydroformylation of n-octene mixtures. However, n-selectivity for nonanal, which is likewise desired, is in need of improvement at 36.8% up to a maximum of 57.6%. This is all the more true in that the use of the catalytically active composition in industrial operations requires a service life measured in days rather than hours.

The literature discloses the synthesis of symmetric bisphosphites as disclosed since U.S. Pat. No. 4,769,498, and the use thereof in catalytically active, transition metal-containing compositions for hydroformylation of unsaturated compounds.

The bisphosphites disclosed in U.S. Pat. No. 5,288,918 in column 8 under the general formula (V) are symmetric bisphosphites. The bisphosphite is symmetric even when $X^1$ and $X^2$ are different radicals, as is the case in the table in column 11 for Ref. No. 2 and 3.

In U.S. Pat. No. 4,769,498, and also in U.S. Pat. No. 5,723,641, preferably symmetric bisphosphites are prepared and used as ligands for hydroformylation. The symmetric bisphosphite ligands used in the hydroformylation are prepared at low temperatures. Compliance with these low temperatures is absolutely necessary, since higher temperatures, according to these US documents, would lead to rearrangements and ultimately to unsymmetric bisphosphites, which is not wanted here.

These unsymmetric bisphosphites, when used as a ligand in transition metal-catalysed hydroformylation, have much lower reactivities and lower n-regioselectivity; see Rhodium-catalyzed Hydroformylation, ed. by P. W. N. M. van Leeuwen and C. Claver, Kluwer Academic Publishers 2006, AA Dordrecht, NL, pages 45-46.

As stated by van Leeuwen, the symmetric bisphosphites, as well as higher selectivities, also have a greater reactivity. Aside from the aim of a high reactivity and n-selectivity in relation to the unsaturated compounds to be carbonylated, the stability—specifically the service life—of the catalytically active composition, composed of the metal, ligands and further components having activating action used in each case, with regard to the bisphosphites used as ligands is a constant task in research. This is especially true with regard to olefin-containing mixtures, specifically in the hydroformylation of mixtures of linear olefins.

U.S. Pat. No. 5,364,950, and also U.S. Pat. No. 5,763,677 and "Catalyst Separation, Recovery and Recycling", edited by D. J. Cole-Hamilton, R. P. Tooze, 2006, NL, pages 25-26, describe the formation of what are called "poisoning phosphites" as secondary reactions or ligand degradation reactions. These "poisoning phosphites" form in the course of use of aryl phosphite-modified rhodium complexes during the hydroformylation reaction. In the course of ligand degradation here, an aryl group is exchanged for an alkyl group in the hydroformylation product.

As well as the formation of the unwanted "poisoning phosphites", the phosphite ligand can also be degraded in the course of a hydrolysis reaction by the water traces formed in aldehyde condensation.

A consequence of these degradation reactions of the ligands is that the concentration of hydroformylation-active rhodium complex species decreases over the course of time and is accompanied by a loss of reactivity.

It is common knowledge that, in a continuous mode of hydroformylation, ligand(s) and optionally further components have to be replenished during the course of the reaction, i.e. have to be added additionally after commencement of the reaction (see DE 10 2008 002 187 A1).

The technical object of the present invention is the provision of novel ligands which do not have the above-detailed disadvantages from the prior art in the hydroformylation of unsaturated compounds, but instead have the following properties:

1.) a high activity, and
2.) a high n-regioselectivity in relation to the hydroformylation and
3.) a high service life.

A high service life means that the hydroformylation-active composition comprising the ligands in addition to further components has a low tendency to degradation of these ligands and/or to decomposition of these ligands to hydroformylation-inhibiting components, for example the "poisoning phosphites".

The object is achieved by a mixture comprising the compounds (Ia) and (IIa):

Mixture comprising the compounds (Ia) and (IIa):

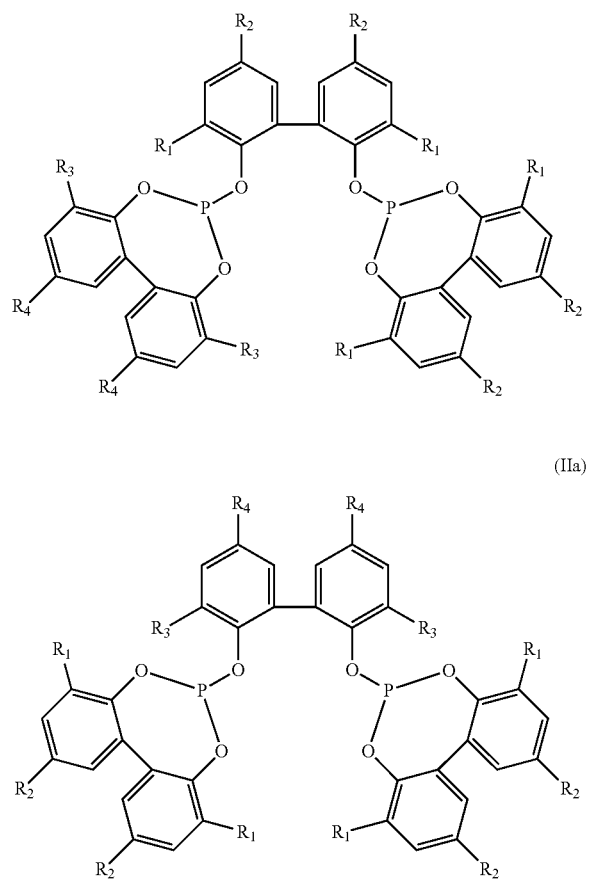

where
R1 is selected from -Me, -tBu, —OMe;
R2 is selected from -Me, -tBu, —OMe;
R3 is selected from -Me, -tBu, —OMe;
R4 is selected from -Me, -tBu, —OMe;
with the proviso that,
if R1 is the same as R3, R2 is not the same as R4,
if R2 is the same as R4, R1 is not the same as R3,
and P can enter into further bonds.

The provisos that if R1 is the same as R3, R2 is not the same as R4, if R2 is the same as R4, R1 is not the same as R3, rule out identical substitution of all three biphenols.

In the case of Ia, an unsymmetric bisphosphite is present, whereas IIa is a symmetric bisphosphite. The mixture thus includes one symmetric and one unsymmetric bisphosphite.

Figure 1:
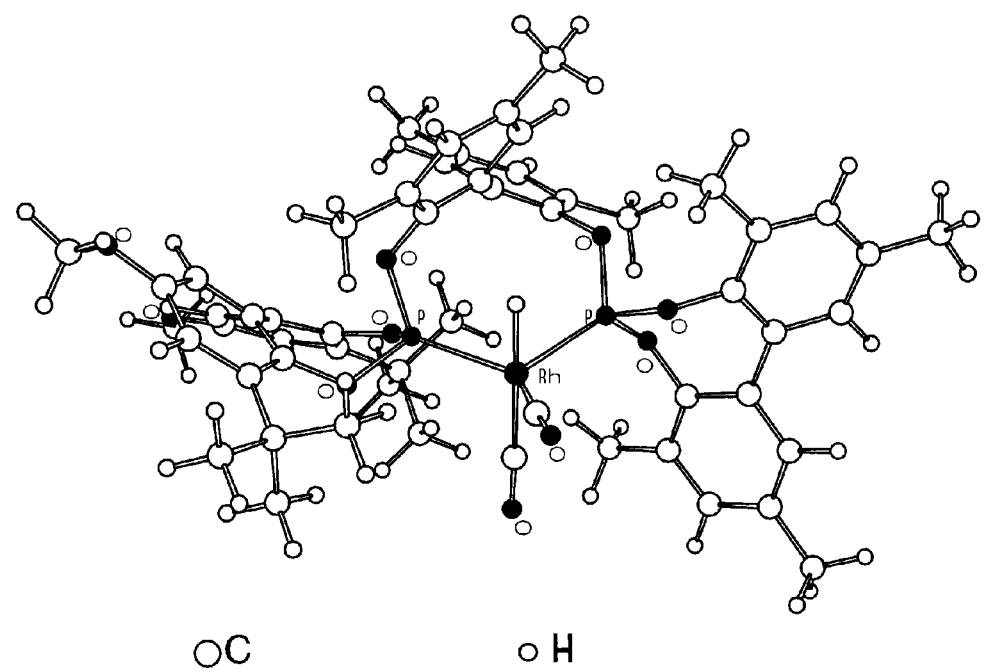
FIG. 1 shows the calculated complex (Ic) where R1=Me, R2=Me, R3=tBu, R4=OMe and M=Rh.

Normally, in the prior art, ligands of maximum purity are used in the hydroformylation reaction, since the other isomer in each case exerts strong adverse effects on the overall performance of the system. In general, the unsymmetric isomer would be present as a secondary component, since exclusively symmetric ligands are used in the hydroformylation.

Rhodium-catalyzed Hydroformylation, ed. by P. W. N. M. van Leeuwen and C. Claver, Kluwer Academic Publishers 2006, AA Dordrecht, NL, pages 45-46, table 2, describes the hydroformylation results for the symmetric biphephos ligand and the unsymmetric isomer thereof. In this context, it is clearly apparent that the symmetric biphephos ligand (in the reference ligand 5a) features a much higher n/i selectivity and a higher activity than its unsymmetric isomer (in the reference ligand 7). In the hydroformylation reaction of propene, the symmetric ligand has an n/i selectivity of 53 and a reaction rate of 402, whereas the unsymmetric ligand has only an n/i selectivity of 1.2 and a reaction rate of 280. If a mixture of the two ligands were then to be used, this would lead to much poorer yields and n/i selectivities. A much poorer overall performance was also recorded with the isomer mixture of ligands (7) and (8). If the inventive isomer mixture is then used in the hydroformylation, this is not the case, and the other isomer can be present as a secondary component in the isomer mixture without adversely affecting the overall performance of the system.

This is particularly advantageous, since no further purification steps are thus necessary during the ligand preparation in order to obtain an isomer with 100% purity. This is particularly favourable, since every further purification step in the ligand preparation makes it more expensive. In general, different solvents are used for these purifications, and different purifications are necessary under some circumstances, for example recrystallizations, and these inevitably lead to product losses. The result of this in turn is that the preparation of the ligand becomes much more expensive, and this in turn has an adverse effect on the overall economic viability of an industrial scale operation. Thus, it is particularly advantageous if it is possible to dispense with costly purification steps and use corresponding isomer mixtures in an industrial scale hydroformylation operation.

In one embodiment, the content of compound (Ia) is within a range from 0.5 to 99.5% by mass, and the content of compound (IIa) within a range from 0.5 to 99.5% by mass.

The two compounds (Ia) and (IIa) add up to 100% by mass.

In one embodiment, the mixture comprises compounds (Ib) and (IIb):

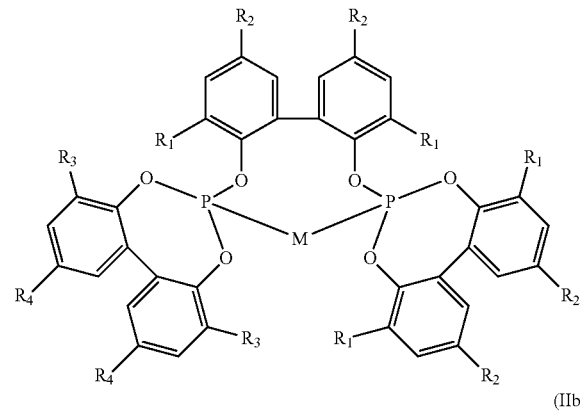

(Ib)

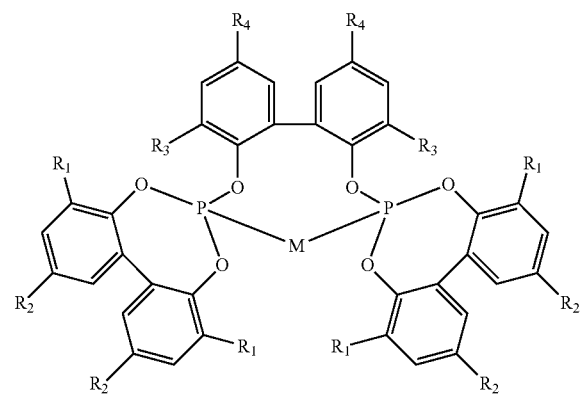

(IIb)

where M is selected from Fe, Ru, Os, Co, Rh, Ir, Ni, Pd, Pt, and M can enter into additional bonds.

In one embodiment, the content of compound (Ib) is within a range from 0.5 to 99.5% by mass, and the content of compound (IIb) within a range from 0.5 to 99.5% by mass.

The two compounds (Ib) and (IIb) add up to 100% by mass.

In one embodiment, the mixture comprises compounds (Ic) and (IIc):

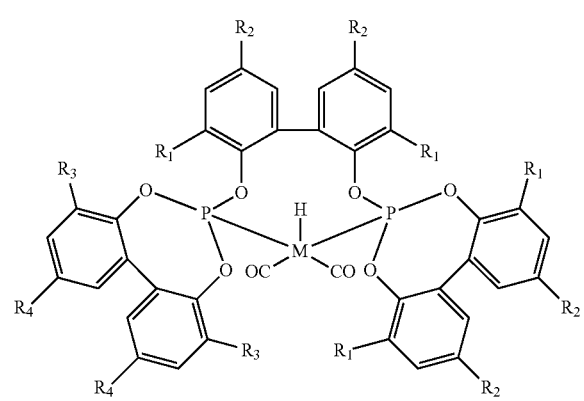

(Ic)

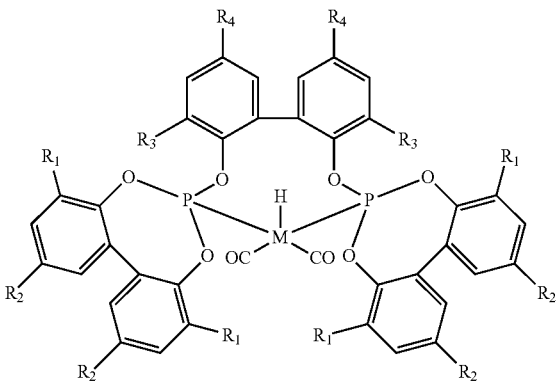

(IIc)

where M is selected from Fe, Ru, Os, Co, Rh, Ir, Ni, Pd, Pt.

In one embodiment, the content of compound Ic is within a range from 0.5 to 99.5% by mass, and the content of compound IIc within a range from 0.5 to 99.5% by mass.

The two compounds Ic and IIc add up to 100% by mass.

In one embodiment, the mixture additionally comprises at least one compound (I) or (IIa) not bonded to M.

In one embodiment, M is Rh.

In one embodiment, R1 is -Me, and R3 is not -Me.

In one embodiment, R2 is -Me, and R4 is not -Me.

In one embodiment, R1 and R2 are each -Me.

In one embodiment, R1 is -tBu, and R3 is not -tBu.

In one embodiment, R2 is —OMe, and R4 is not —OMe.

The different mixtures may either originate directly from the synthesis, meaning that the two isomers (Ia) and (IIa) are generated during one and the same synthesis, or be mixed from the pure compounds of the formulae (Ia) and (IIa) after the synthesis.

In a preferred embodiment, the compounds have the structures (1Ia) and (2IIa):

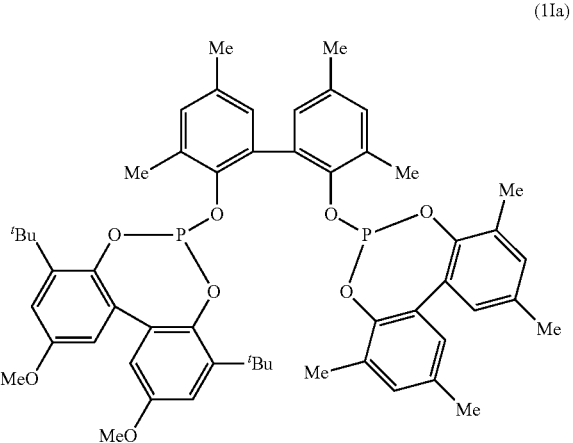

(1Ia)

(2IIa)

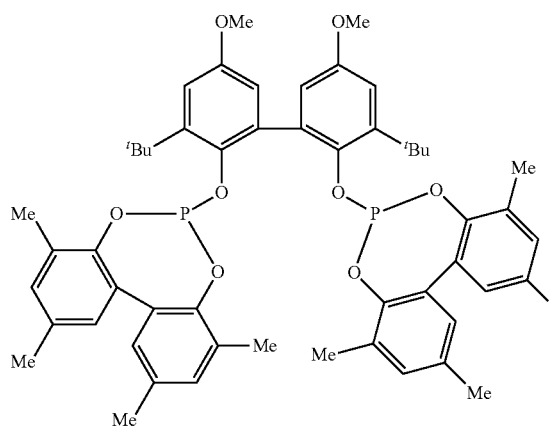

In a further preferred embodiment, the compounds have the structures (3Ia) and (4IIa):

(3Ia)

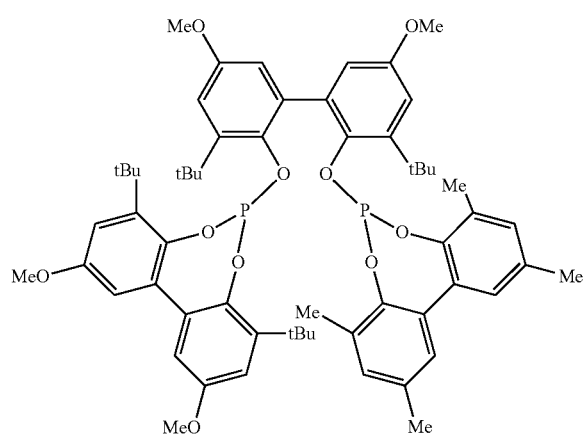

(4IIa)

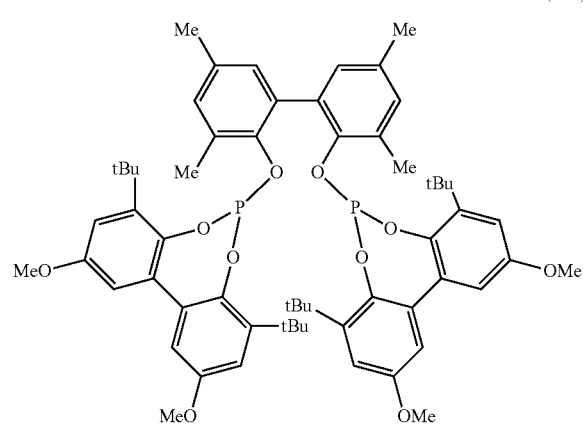

By way of example for the various R radicals, the compounds (1Ia), (2IIa), (3Ia) and (4IIa) are summarized in Table 1 below.

TABLE 1

|  | Isomer | R1 | R2 | R3 | R4 |
|---|---|---|---|---|---|
| (1Ia) | (Ia) | —Me | —Me | —tBu | —OMe |
| (2IIa) | (IIa) | —Me | —Me | —tBu | —OMe |
| (3Ia) | (Ia) | —tBu | —OMe | —Me | —Me |
| (4IIa) | (IIa) | —tBu | —OMe | —Me | —Me |

The invention encompasses the following subjects:
a) mixtures of bisphosphites of the formulae (Ia) and (IIa);
b) processes for preparation thereof;
c) metal mixtures of the formulae (Ib) and (IIb), where M is a metal from groups 4 to 10 of the Periodic Table of the Elements (Fe, Ru, Os, Co, Rh, Ir, Ni, Pd, Pt) and can enter into additional bonds, and the constitutional isomers of the formulae (Ia) and (IIa) not bonded to the metal M are present;

(Ib)

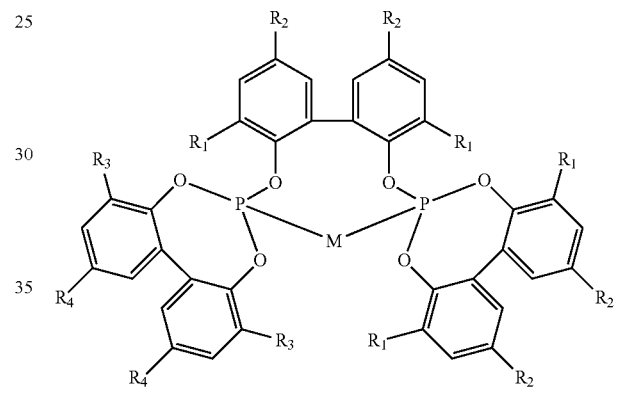

(IIb)

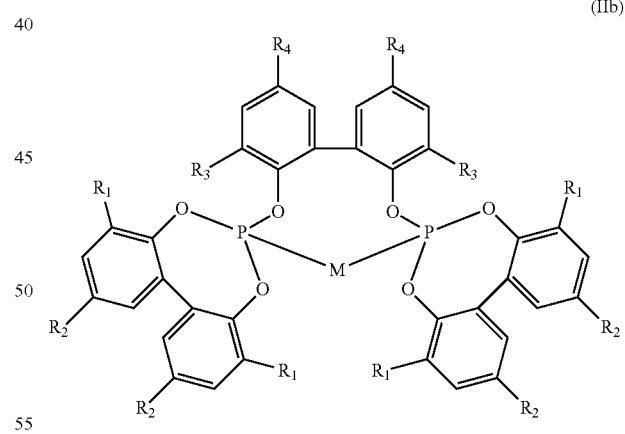

where M is selected from Fe, Ru, Os, Co, Rh, Ir, Ni, Pd, Pt, and M can enter into additional bonds.
d) compositions comprising the constitutional isomers mentioned under a), metals from groups 4 to 10 of the Periodic Table of the Elements (Fe, Ru, Os, Co, Rh, Ir, Ni, Pd, Pt) and free, i.e. unbound, bisphosphites of the formulae (1a) and (2a) and at least one further component selected from the group comprising bases, organic amines, epoxides, ion exchangers, buffer systems;
e) processes for hydroformylating unsaturated compounds and mixtures thereof using compositions according to d), a gas mixture consisting of carbon monoxide and hydrogen, unsaturated compounds and mixtures thereof under the reaction conditions required for a hydroformylation;

f) polyphasic reaction mixture consisting of:

f1) at least one composition according to d);

f2) a gas mixture comprising carbon monoxide and hydrogen;

f3) at least one unsaturated compound as substrate and;

f4) at least one hydroformylation product formed from the substrates.

As well as the mixture, a composition comprising such a mixture is also claimed.

Composition comprising:

an above-described mixture, a further component selected from: bases, organic amines, epoxides, buffer solutions, ion exchangers.

In a preferred embodiment, further components used are sterically hindered secondary amines.

It is also possible to use mixtures comprising two or more sterically hindered amines.

The composition comprises an above-described mixture including, in addition to the mixture, at least one amine having a 2,2,6,6-tetramethylpiperidine unit.

More particularly, in the process according to the invention, the amine having the formula (11), di-4-(2,2,6,6-tetramethylpiperidinyl) sebacate, is used with preference.

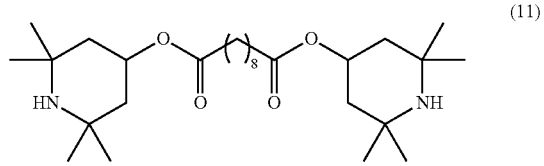

(11)

A particularly preferred metal in the inventive composition is rhodium.

As well as the mixture, a process for preparation thereof is also claimed.

Process for preparing an above-described mixture, comprising the process steps of:

a) oxidative coupling according to reaction scheme A:

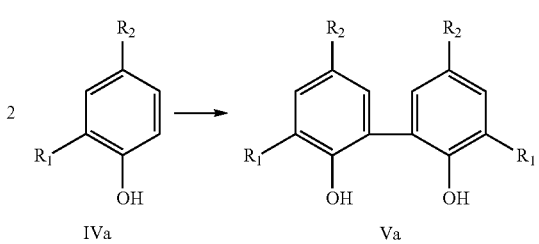

A b) oxidative coupling according to reaction scheme B:

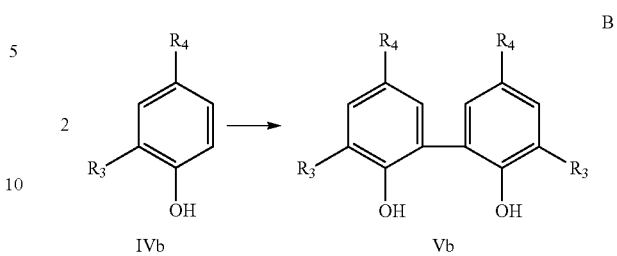

B c) reaction of the product from a) with PCl$_3$ according to reaction scheme C:

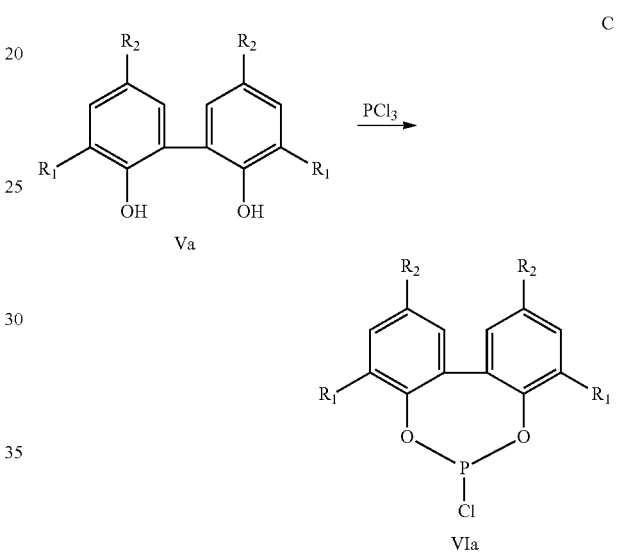

C d) reaction of the product from b) with the product from c) to give a mixture according to claim 1.

A particular advantage of the present invention lies in the use of the above-described mixtures (Ia) and (IIa), especially (1Ia) and (2IIa), in the hydroformylation, because the inventive use of the mixture of the constitutionally isomeric bisphosphites rather than a pure compound obviates the need for an inconvenient and costly separation of the constitutional bisphosphite compounds.

From the prior art, a lowered reactivity and lower n/i selectivity are expected because of the presence of the unsymmetric bisphosphite (Ia), especially the derivative thereof (Ic). As disclosed in the hydroformylation experiments which follow, the bisphosphite compounds (1Ia) and (2IIa) surprisingly have, as well as high reactivities and n/i selectivities, a distinctly increased service life compared to the bisphosphites known from the prior art.

In one embodiment, the process additionally comprises the process step of:

e) reaction with M to give (Ib) and (IIb), where M is selected from Fe, Ru, Os, Co, Rh, Ir, Ni, Pd, Pt.

Additionally claimed is also the use of the mixture as a catalyst in a hydroformylation reaction of unsaturated compounds and mixtures thereof. The wording "as a catalyst" should be understood here such that the compounds are used as ligands for a metal complex, which then catalyses the corresponding reaction.

These defined mixtures of the bisphosphites, consisting of the compounds of the formula (Ia) and (IIa), can, for example, be initially charged directly at the start of a hydroformylation reaction. This procedure thus differs from the general method in a stability study, in which a defined isomer is initially charged and the further compounds form only in the course of the reaction.

Additionally claimed is a process for hydroformylating unsaturated compounds and mixtures thereof.

Process for hydroformylating unsaturated compounds and mixtures thereof using:
i) an above-described composition,
ii) a gas mixture comprising carbon monoxide and hydrogen.

The unsaturated compounds which are hydroformylated in the process according to the invention include hydrocarbon mixtures obtained in petrochemical processing plants. Examples of these include what are called $C_4$ cuts. Typical compositions of $C_4$ cuts from which the majority of the polyunsaturated hydrocarbons has been removed and which can be used in the process according to the invention are listed in table 1 below (see DE 10 2008 002188).

In a particular variant of the process, the mixture includes unsaturated compounds having 2 to 8 carbon atoms.

In a further variant of the process, the mixture includes polyunsaturated hydrocarbons. In a particular embodiment, the mixture comprises butadiene.

The unsaturated compounds which are hydroformylated in the process according to the invention additionally include unsaturated carboxylic acid derivatives. In a particular embodiment, these unsaturated carboxylic acid derivatives are selected from fatty acid esters.

The process according to the invention is performed in different embodiments which are disclosed in detail in the examples.

The inventive polyphasic reaction mixture comprises, as well as a gas mixture consisting of carbon monoxide and hydrogen, at least one unsaturated compound as disclosed above, and comprises, as well as hydrocarbon mixtures which originate from steamcracking, catalytically operated cracking plants or oligomerization operations, or contain other sources of monounsaturated and/or polyunsaturated carbon compounds or unsaturated carboxylic acid derivatives, at least one hydroformylation product of these unsaturated com-

TABLE 2

| | Steamcracking plant | | Steamcracking plant | | Catalytic cracking plant | |
|---|---|---|---|---|---|---|
| Component | $HCC_4$ | $HCC_4$/SHP | Raff. I | Raff. I/SHP | $CC_4$ | $CC_4$/SHP |
| isobutane [% by mass] | 1-4.5 | 1-4.5 | 1.5-8 | 1.5-8 | 37 | 37 |
| n-butane [% by mass] | 5-8 | 5-8 | 6-15 | 6-15 | 13 | 13 |
| E-2-butene [% by mass] | 18-21 | 18-21 | 7-10 | 7-10 | 12 | 12 |
| 1-butene [% by mass] | 35-45 | 35-45 | 15-35 | 15-35 | 12 | 12 |
| isobutene [% by mass] | 22-28 | 22-28 | 33-50 | 33-50 | 15 | 15 |
| Z-2-butene [% by mass] | 5-9 | 5-9 | 4-8 | 4-8 | 11 | 11 |
| 1,3-butadiene [ppm by mass] | 500-8000 | 0-50 | 50-8000 | 0-50 | <10000 | 0-50 |

Key:
$HCC_4$: typical of a $C_4$ mixture which is obtained from the $C_4$ cut from a steamcracking plant (high severity) after the hydrogenation of the 1,3-butadiene without additional moderation of the catalyst.
$HCC_4$/SHP: $HCC_4$ composition in which residues of 1,3-butadiene have been reduced further in a selective hydrogenation process/SHP.
Raff. I (raffinate I): typical of a $C_4$ mixture which is obtained from the $C_4$ cut from a steamcracking plant (high severity) after the removal of the 1,3-butadiene, for example by an NMP extractive rectification.
Raff. I/SHP: raff. I composition in which residues of 1,3-butadiene have been reduced further in a selective hydrogenation process/SHP.
$CC_4$: typical composition of a $C_4$ cut which is obtained from a catalytic cracking plant.
$CC_4$/SHP: composition of a $C_4$ cut in which residues of 1,3-butadiene have been reduced further in a selective hydrogenation process/SHP.

In one variant of the process, the unsaturated compound or mixture thereof has been selected from:
hydrocarbon mixtures from steamcracking plants;
hydrocarbon mixtures from catalytically operated cracking plants, for example FCC cracking plants;
hydrocarbon mixtures from oligomerization operations in homogeneous phase and heterogeneous phases, for example the OCTOL, DIMERSOL, Fischer-Tropsch, Polygas, CatPoly, InAlk, Polynaphtha, Selectopol, MOGD, COD, EMOGAS, NExOCTANE or SHOP process;
hydrocarbon mixtures comprising polyunsaturated compounds;
unsaturated carboxylic acid derivatives.

In one variant of the process, the mixture includes unsaturated compounds having 2 to 30 carbon atoms.

pounds as detailed in the examples which follow, and the composition used in each case, as disclosed above.

FIG. 1 shows the calculated complex (Ic) where R1=Me, R2=Me, R3=tBu, R4=OMe and M=Rh.

The inventive complexes of the formulae (Ic) and (11c) are formed in situ during the hydroformylation reaction.

In a particular embodiment of the invention, the complexes (Ic) and (11c) are present alongside the unbound bisphosphite.

The hydridocarbonyl complex Ic with rhodium as the metal was characterized by means of theoretical calculations. The result is shown in FIG. 1.

The structure calculation was conducted with the BP86 functional and the def-SV(P) base set.

The structure calculations for the model structures were effected with the Turbomole program package (R. Ahlrichs, M. Bar, M. Haser, H. Horn, C. Kolmel, Chem. Phys. Lett., 1989, 162, 16; TURBOMOLE V6.3 2011, a development of University of Karlsruhe and Forschungszentrum Karlsruhe GmbH, 1989-2007, TURBOMOLE GmbH, since 2007. http://www.turbomole.com) on the basis of density functional theory (DFT). The BP86 functional (S. H. Vosko, L. Wilk, M. Nusair, Can. J. Phys., 1980, 58, 1200; A. D. Becke, Phys. Rev. A, 1988, 38, 3098; J. Perdew, Phys. Rev. B, 1986, 33, 8822) and the def-SV(P) base set (A. Schafer, H. Horn and R. Ahlrichs, J. Chem. Phys., 1992, 97, 2571) were used.

EXAMPLES

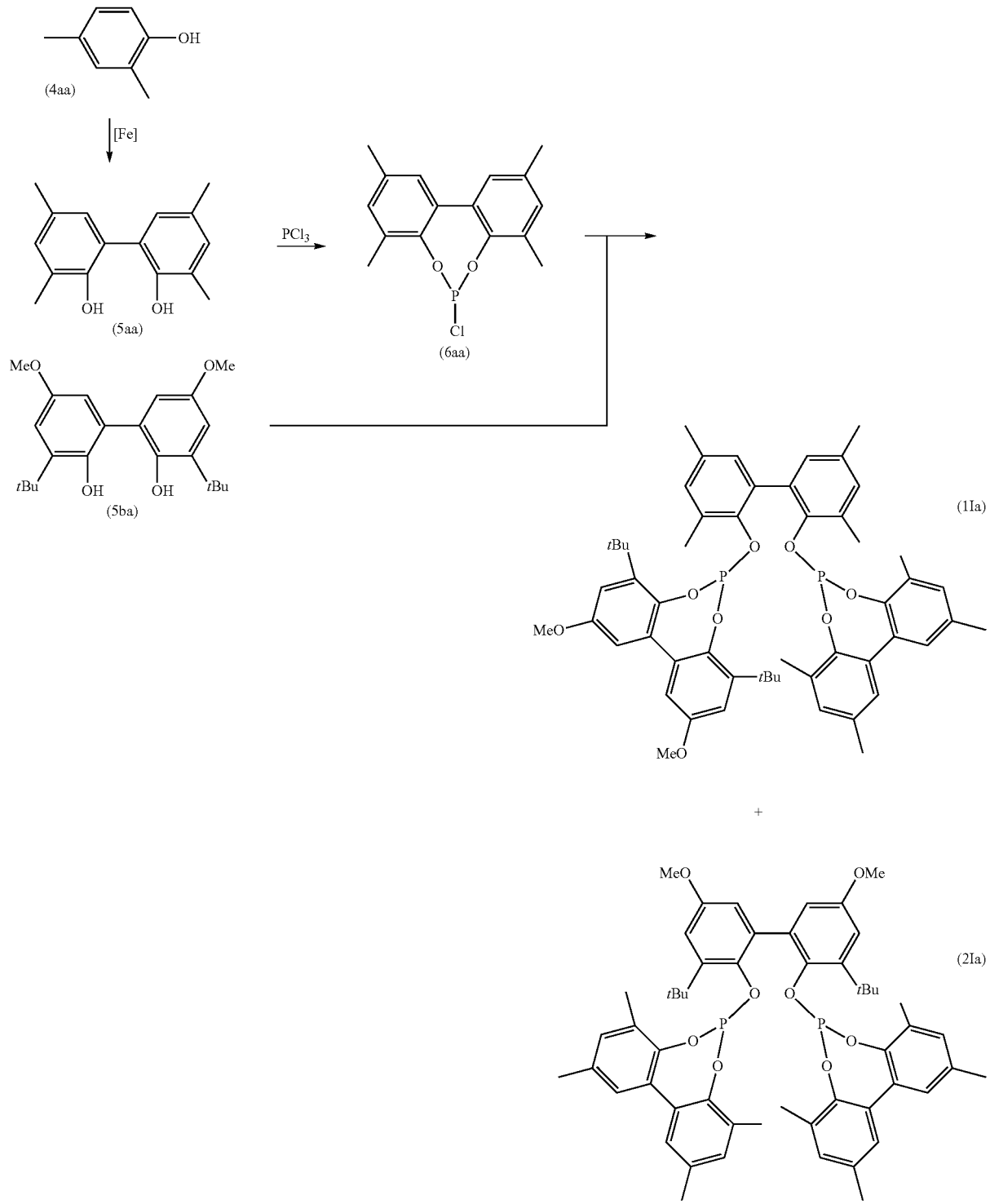

ABBREVIATIONS

DM water=demineralized water
CPG=core-pulled precision glass
ACN=acetonitrile
EtOAc=ethyl acetate
DMAB=dimethylaminobutane
NMP=N-methylpyrrolidone
OV=oil vacuum
acac=acetylacetonate
$NEt_3$=triethylamine
TIPB=1,2,4,5-tetraisopropylbenzene Synthesis of 2,2'-bis(3,5-dimethylphenol) (5aa)

The biphenol (5aa) used as a precursor was prepared by the synthesis method which follows.

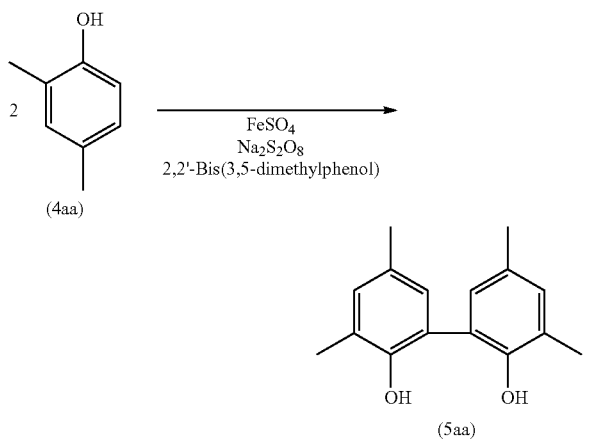

A 500 ml Schlenk with CPG stirrer, intermediate section and glass stirrer was initially charged with 1.42 g (0.005 mol) of iron(II) sulphate heptahydrate and 12.35 g (0.1 mol) of 2,4-dimethylphenol in 150 ml of DM water and 5 ml of cyclohexane, and the mixture was heated to 40° C.

In a 100 ml beaker, 25.36 g (0.146 mol) of sodium peroxodisulphate were dissolved in 80 ml of DM water. At the start of the reaction, a small portion of $Na_2S_2O_8$ solution was added to the phenol. Subsequently, a smaller portion of the solution was added every 10 min. After 30 min, the $Na_2S_2O_8$ solution had been added.

After a reaction time of 5 h, 300 ml of cyclohexane and 200 ml of water were added to the reaction solution, which was left to stir for 20 min, then transferred while warm into a separating funnel.

The organic phase was removed and concentrated to dryness. The product was obtained in 69% yield (10.6 g).

All the preparations which follow were conducted with standard Schlenk technology under protective gas. The solvents were dried over suitable desiccants before use (Purification of Laboratory Chemicals, W. L. F. Armarego (Author), Christina Chai (Author), Butterworth Heinemann (Elsevier), 6th edition, Oxford 2009).

The product was characterized by means of NMR spectroscopy. Chemical shifts are reported in ppm. The $^{31}P$ NMR signals were referenced according to: $SR_{31P}=SR_{1H}*(BF_{31P}/BF_{1H})=SR_{1H}*0.4048$. (Robin K. Harris, Edwin D. Becker, Sonia M. Cabral de Menezes, Robin Goodfellow, and Pierre Granger, Pure Appl. Chem., 2001, 73, 1795-1818; Robin K. Harris, Edwin D. Becker, Sonia M. Cabral de Menezes, Pierre Granger, Roy E. Hoffman and Kurt W. Zilm, Pure Appl. Chem., 2008, 80, 59-84). By means of $^{31}P$ NMR, the ratio of the two ligands (ligand 1Ia and ligand 2IIa) to one another was determined. The unsymmetric ligand (1Ia) is characterized by two phosphorus signals, whereas only one phosphorus signal is to be expected for the symmetric ligand (2IIa).

Synthesis of
2,2'-bis(3,5-dimethylphenol)chlorophosphite

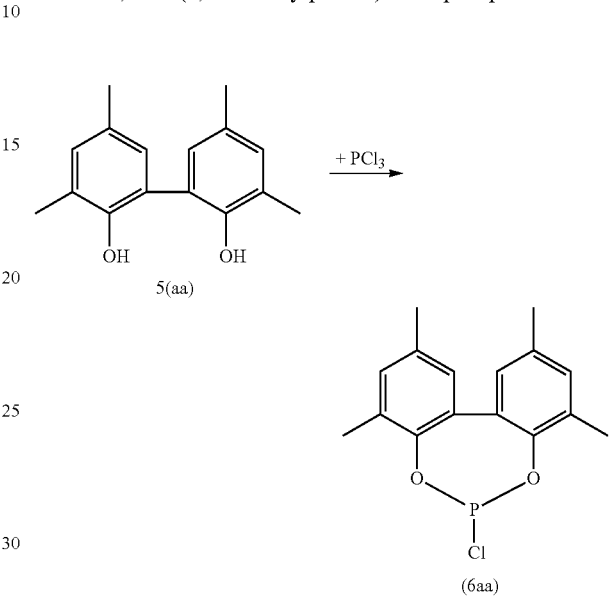

A secured 2 l Schlenk with magnetic stirrer was initially charged with 440 ml of phosphorus trichloride. 120 g of 2,2-bis(3,5-dimethylphenol) were weighed into a second secured 1 l Schlenk and 500 ml of dried toluene were added while stirring. The biphenol-toluene suspension was metered into the phosphorus trichloride at 63° C. within 4 h. On completion of addition, the reaction mixture was stirred at temperature overnight. The next morning, the solution was concentrated while warm (45° C.), and the product was obtained in 96.5% yield (153 g). $^{31}P$ NMR: 175.59 (94.8% 2,2'-bis(3,5-dimethylphenol)chlorophosphite), 4.4% various PCI compounds, 0.8% P—H compound.

Inventive Synthesis Variations for Preparation of the Mixture of Ligands (1Ia) and (2IIa)

Variant 1: ACN/$NEt_3$

In a 1000 ml Schlenk, under protective gas, 38.75 g (0.121 mol) of 2,2'-bis(3,5-dimethylphenol)chlorophosphite were dissolved in 150 ml of degassed ACN and heated to 35° C. In a second Schlenk (500 ml), 20.1 g (0.056 mol) of 3,3'-di-tert-butyl-5,5'-dimethoxy-[1,1'-biphenyl]-2,2'-diol were dissolved in 150 ml of degassed ACN, and 40.9 ml of degassed triethylamine (0.29 mol) were added while stirring. Then the biphenol/triethylamine solution was slowly added dropwise to the chlorophosphite solution.

After a further reaction time of 1 h, the reaction solution was stirred at 45° C. overnight.

Subsequently, the solution was filtered and the solids were washed three times with 100 ml of warm (45° C.) ACN. The target product was obtained as a white solid (43.3 g, 86%). $^{31}P$ NMR (202.4 MHz, toluene-$d_8$): 142.5 and 140.9 (95.4%) 139.2 (4.6%).

Variant 2: EtOAc/NEt₃

In a 100 ml Schlenk, under protective gas, 7.3 g (21.0 mmol) of 2,2'-bis(3,5-dimethylphenol)chlorophosphite were dissolved in 15 ml of degassed ethyl acetate and heated to 35° C. In a second Schlenk (100 ml), 3.9 g (9.5 mmol) of 3,3'-di-tert-butyl-5,5'-dimethoxy-[1,1'-biphenyl]-2,2'-diol were suspended in 7.0 ml of NEt₃. Subsequently, the biphenol/triethylamine solution was slowly added dropwise to the chlorophosphite solution within 20 minutes. The solution was stirred at 35° C. for a further hour and then at 45° C. overnight.

The next day, the solution was filtered and the solids were washed three times with ACN. The target product was obtained as a white solid (6.7 g, 78%). $^{31}$P NMR (202.4 MHz, toluene-d₈): 142.5 and 140.9 (91.3%), 139.5 (8.7%).

Variant 3: EtOAc/pyridine

In a 250 ml Schlenk, under protective gas, 10.07 g (31.0 mmol) of 2,2'-bis(3,5-dimethylphenol)chlorophosphite were dissolved in 20 ml of degassed ethyl acetate and heated to 45° C. In a second Schlenk (50 ml), 5.54 g (15 mmol) of 3,3'-di-tert-butyl-5,5'-dimethoxy-[1,1'-biphenyl]-2,2'-diol were dissolved in 26 ml of ethyl acetate and 5.2 ml of degassed pyridine. Subsequently, the biphenol/pyridine solution was slowly added dropwise to the chlorophosphite solution within 30 minutes. The solution was stirred at 45° C. overnight.

The next day, the solution was filtered and the solids were washed with ACN. The target product was obtained as a white solid (4.2 g, 31%). $^{31}$P NMR (202.4 MHz, toluene-d₈): 142.2 and 141.1 (100%).

Variant 4: ACN/DMAB (dimethylaminobutane)

In a 100 ml Schlenk, under protective gas, 6 g (19.0 mmol) of 2,2'-bis(3,5-dimethylphenol)chlorophosphite were dissolved in 20 ml of degassed ACN and heated to 35° C. In a second Schlenk (50 ml), 3.4 g (9.0 mmol) of 3,3'-di-tert-butyl-5,5'-dimethoxy-[1,1'-biphenyl]-2,2'-diol were dissolved in 15 ml of dimethylaminobutane (DMAB) and then slowly added dropwise to the chlorophosphite solution. The reaction was left to stir at 35° C. overnight.

The next day, the solution was filtered and the solids were washed twice with ACN. The target product was obtained as a white solid (5.3 g, 66%). $^{31}$P NMR (202.4 MHz, toluene-d₈): 142.8 and 141.2 (97.5%), 139.4 (2.5%).

Variant 5: ACN/NMP (N-methylpyrrolidone)

In a 100 ml Schlenk, under protective gas, 6 g (19.0 mmol) of 2,2'-bis(3,5-dimethylphenol)chlorophosphite were dissolved in 20 ml of degassed ACN and heated to 35° C. In a second Schlenk (50 ml), 3.4 g (9.0 mmol) of 3,3'-di-tert-butyl-5,5'-dimethoxy-[1,1'-biphenyl]-2,2'-diol were dissolved in 9.4 ml of N-methylpyrrolidone (NMP) and slowly added dropwise to the chlorophosphite solution. The reaction was left to stir at 35° C. overnight.

Subsequently, the solution was filtered and the solids were washed twice with ACN. The target product was obtained as a white solid (3.4 g, 42%). $^{31}$P NMR (202.4 MHz, toluene-d₈): 142.2 and 141.0 (96.1%), 139.8 (3.9%).

Variant 6: ACN/diisopropylethylamine

In a 500 ml Schlenk, under protective gas, 19.4 g (61.0 mmol) of 2,2'-bis(3,5-dimethylphenol)chlorophosphite were suspended in 75 ml of degassed ACN. In a second Schlenk (250 ml), 10.5 g (28.5 mmol) of 3,3'-di-tert-butyl-5,5'-dimethoxy-[1,1'-biphenyl]-2,2'-diol were suspended in 75 ml of acetonitrile and 39 ml of diisopropylamine, and added gradually to the chlorophosphite solution. The reaction was left to stir overnight.

Subsequently, the solution was filtered and the solids were washed three times with ACN. The target product was obtained as a white solid (14.6 g, 57%). $^{31}$P NMR (202.4 MHz, toluene-d₈): 142.2 and 141.1 (76.8%), 139.1 (23.2%).

Variant 7: toluene/NEt₃

In a 100 ml Schlenk, under protective gas, 7.7 g (24.0 mmol) of 2,2'-bis(3,5-dimethylphenol)chlorophosphite were dissolved in 15 ml of degassed toluene and heated to 35° C. In a second Schlenk (50 ml), 3.4 g (9.0 mol) of 3,3'-di-tert-butyl-5,5'-dimethoxy-[1,1'-biphenyl]-2,2'-diol were dissolved in 15 ml of dimethylaminobutane (DMAB) and slowly added dropwise to the chlorophosphite solution. The reaction was left to stir at 45° C. for 4 days. Thereafter, the solution, after further addition of 120 ml of toluene, was heated to 75° C. for 30 minutes.

Subsequently, the solution was filtered, and the filtrate was concentrated to dryness and dried. The target product was obtained as a white solid (7.2 g, 88%). $^{31}$P NMR (202.4 MHz, toluene-d₈): 142.5 and 140.9 (91.4%), 139.2 (8.6%).

Variant 8: Variation in the amount of amine (ACN/NEt₃)

A: In a 500 ml Schlenk, under protective gas, 17.81 g (0.073 mol) of 2,2'-bis(3,5-dimethylphenol)chlorophosphite were added to 60 ml of degassed ACN and heated to 35° C. In a second Schlenk (250 ml), 9.91 g (0.0276 mol) of 3,3'-di-tert-butyl-5,5'-dimethoxy-[1,1'-biphenyl]-2,2'-diol were dissolved in 60 ml of degassed ACN, and 38.4 ml of degassed triethylamine were added while stirring. This biphenol/triethylamine solution was then slowly added dropwise to the chlorophosphite solution. After a further reaction time of 1 h, the reaction solution was stirred at 35° C. overnight.

Subsequently, the solution was filtered and the solids were washed with ACN. The target product was obtained as a white solid (27.8 g, 86%). $^{31}$P NMR (202.4 MHz, toluene-d₈): 142.8 and 141.2 (91.6%), 139.4 (8.4%).

B: In a 250 ml Schlenk, under protective gas, 1.57 g (5.1 mmol) of 2,2'-bis(3,5-dimethylphenol)chlorophosphite were added to 7 ml of degassed ACN and heated to 35° C. In a second Schlenk (100 ml), 0.932 g (2.6 mmol) of 3,3'-di-tert-butyl-5,5'-dimethoxy-[1,1'-biphenyl]-2,2'-diol were dissolved in 9 ml of degassed ACN, and 2.09 ml of degassed triethylamine were added while stirring. Then the biphenol/triethylamine solution was slowly added dropwise to the chlorophosphite solution. After a further reaction time of 1 h, the reaction solution was stirred at 35° C. overnight.

Subsequently, the solution was filtered and the solids were washed with ACN. The target product was obtained as a white solid in 40% yield. $^{31}$P NMR (202.4 MHz, toluene-d₈): 142.8 and 141.8 (92.4%), 139.3 (7.6%).

Variant 9: Shortened reaction times

A (8 hours): EtOAc/NEt₃

In a 100 ml Schlenk, under protective gas, 8 g (25.0 mmol) of 2,2'-bis(3,5-dimethylphenol)chlorophosphite were dissolved in 20 ml of degassed ethyl acetate and heated to 45° C. In a second Schlenk (50 ml), 4.48 g (12.5 mmol) of 3,3'-di-tert-butyl-5,5'-dimethoxy-[1,1'-biphenyl]-2,2'-diol were suspended in 20 ml of ethyl acetate and 8.0 ml of NEt₃. Subsequently, the biphenol/triethylamine suspension was slowly added dropwise to the chlorophosphite solution within 30 minutes. The solution was stirred at 45° C. for eight hours. Subsequently, the solution was filtered. The target product was obtained as a white solid (12.26 g, 84.7%). $^{31}$P NMR (202.4 MHz, toluene-d₈): 142.2 and 141.1 (88.1), 139.1 (11.9).

B (4 hours): EtOAc/NEt₃

In a 100 ml Schlenk, under protective gas, 10.07 g (31.0 mmol) of 2,2'-bis(3,5-dimethylphenol)chlorophosphite were dissolved in 20 ml of degassed ethyl acetate and heated to 45° C. In a second Schlenk (50 ml), 5.54 g (15 mmol) of 3,3'-di-tert-butyl-5,5'-dimethoxy-[1,1'-biphenyl]-2,2'-diol were suspended in 26 ml of ethyl acetate and 9.0 ml of NEt₃. Subsequently, the biphenol/triethylamine suspension was slowly added dropwise to the chlorophosphite solution within 30 minutes. The solution was stirred at 45° C. for four hours.

Subsequently, the solution was filtered and the solids were washed twice with ACN. The target product was obtained as a white solid (6.4 g, 47%). $^{31}$P NMR (202.4 MHz, toluene-$d_8$): 142.2 and 141.1 (99.3%), 139.1 (0.7%).

C (4 hours): ACN/pyridine

In a 250 ml Schlenk, under protective gas, 10 g (31.0 mmol) of 2,2'-bis(3,5-dimethylphenol)chlorophosphite were dissolved in 40 ml of degassed ACN and heated to 45° C. In a second Schlenk (50 ml), 5.5 g (15.0 mmol) of 3,3'-di-tert-butyl-5,5'-dimethoxy-[1,1'-biphenyl]-2,2'-diol were dissolved in 40 ml of ACN and 8.8 ml of pyridine. Then the clear biphenol/pyridine solution formed was slowly added dropwise to the chlorophosphite solution within 30 minutes. After a reaction time of 4 hours, the solution was filtered and the solids were washed twice with ACN. The target product was obtained as a white solid (8.5 g, 63%). $^{31}$P NMR (202.4 MHz, toluene-$d_8$): 142.2 and 141.1 (98.4%), 139.4 (1.6%).

Variant 10: Low-temperature experiments (ACN/NEt$_3$)

A: In a 250 ml Schlenk, under protective gas, 8.0 g (0.025 mol) of 2,2'-bis(3,5-dimethylphenol)chlorophosphite were dissolved in 30 ml of degassed ACN and cooled to −40° C. In a second Schlenk (100 ml), 4.32 g (0.012 mol) of 3,3'-di-tert-butyl-5,5'-dimethoxy-[1,1'-biphenyl]-2,2'-diol were dissolved in 30 ml of degassed ACN, and 8.5 ml of degassed triethylamine were added while stirring. Then the biphenol/triethylamine solution was slowly added dropwise to the chlorophosphite solution. After a further reaction time of 1 h, the reaction solution was brought gradually to room temperature overnight.

Subsequently, the solution was filtered and the solids were washed with cold ACN. The target product was obtained as a white solid (8.9 g, 82%). $^{31}$P NMR (202.4 MHz, toluene-$d_8$): 142.5 and 140.9 (98.4%), 139.4 (1.6%).

Variant 11: Performance at various reaction temperatures (ACN/pyridine)

A: In a 250 ml Schlenk, under protective gas, 9.4 g (28.8 mmol) of 2,2'-bis(3,5-dimethylphenol)chlorophosphite were dissolved in 100 ml of degassed ACN. In a second Schlenk (100 ml), 5.0 g (14.4 mmol) of 3,3'-di-tert-butyl-5,5'-dimethoxy-[1,1'-biphenyl]-2,2'-diol were suspended in 8.8 ml of pyridine. Then the biphenol/pyridine solution was slowly added dropwise to the chlorophosphite solution within 1.5 hours. The solution was stirred at room temperature for a further 2 hours and then at 60° C. overnight. Subsequently, the solution was filtered and the solids were washed twice with ACN. The target product was obtained as a white solid (9.5 g, 73%). $^{31}$P NMR (202.4 MHz, toluene-$d_8$): 142.8 and 141.2 (90%), 139.5 (10%).

B: In a 250 ml Schlenk, under protective gas, 10 g (31.0 mmol) of 2,2'-bis(3,5-dimethylphenol)chlorophosphite were dissolved in 40 ml of degassed ACN and heated to 45° C. In a second Schlenk (50 ml), 5.5 g (15.0 mmol) of 3,3'-di-tert-butyl-5,5'-dimethoxy-[1,1'-biphenyl]-2,2'-diol were dissolved in 40 ml of ACN and 8.8 ml of pyridine. Then the clear biphenol/pyridine solution formed was slowly added dropwise to the chlorophosphite solution within 30 minutes. The solution was stirred at 45° C. overnight. The next morning, the solution was filtered and the solids were washed twice with ACN. The target product was obtained as a white solid (9.5 g, 72%). $^{31}$P NMR (202.4 MHz, toluene-$d_8$): 142.2 and 141.1 (89.9%), 139.1 (10.1%).

Comparative Example, Variant 12: "One-Pot Synthesis"

A secured 250 ml Schlenk was initially charged with 8.45 g (0.0335 mol) of 2,2'-bis(3,5-dimethylphenol) and 5.95 g (0.0166 mol) of 3,3'-di-tert-butyl-5,5'-dimethoxy-[1,1'-biphenyl]-2,2'-diol, which were suspended in 50 ml of dried toluene while stirring. Then 7.1 g (0.051 mol) of phosphorus trichloride and 0.1 ml (0.001 mol) of pyridine were added successively at 0° C. to the suspension and this suspension was brought to room temperature (=RT) within 60 minutes. The reaction mixture was subsequently heated to 35° C. and stirred at this temperature overnight.

In the morning, by means of OV at RT, the excess phosphorus trichloride and the solvent were removed. Thereafter, 25 ml of degassed ACN were added while stirring and the solution was cooled to 0° C. A second Schlenk (50 ml) was initially charged with 25 ml of degassed ACN, and 10.2 g=14 ml (0.1 mol) of triethylamine were added while stirring. The resulting solution was added dropwise to the cooled reaction mixture within 45 min. Then the mixture was warmed up to RT while stirring overnight. In the morning, the solids were filtered off and washed with 2×25 ml of degassed ACN. The desired target product was obtained in 77% yield (13 g). $^{31}$P NMR (202.4 MHz, toluene-$d_8$): 142.2 and 141.1 (96.4%), 139.2 (3.6%).

Influence of the Base/Base Mixture

General Synthesis Method

In a 1000 ml Schlenk, under protective gas, 38.75 g (0.121 mol) of 2,2'-bis(3,5-dimethylphenol)chlorophosphite were dissolved in 150 ml of degassed ACN and heated to 45° C. In a second Schlenk (500 ml), 20.1 g (0.056 mol) of 3,3'-di-tert-butyl-5,5'-dimethoxy-[1,1'-biphenyl]-2,2'-diol were dissolved in 150 ml of degassed ACN, and the appropriate base (the amount used is based on the chlorophosphite) was added while stirring. Then the biphenol/base solution was slowly added dropwise to the chlorophosphite solution. After a further reaction time of 1 h, the reaction solution was stirred at 45° C. overnight. (Other temperatures or reaction times can be found in the tables.)

Synthesis route:

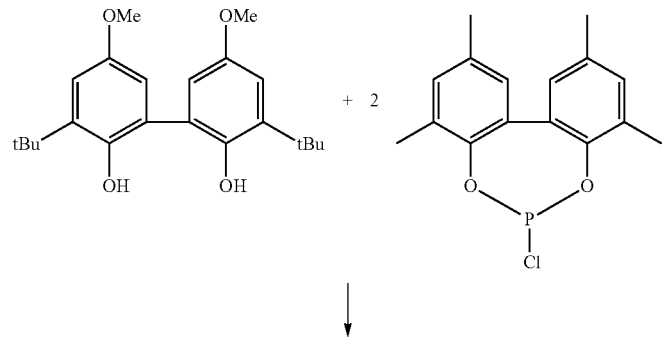

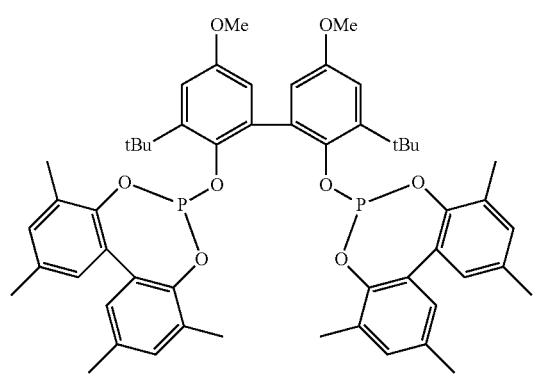

Ligand 2a

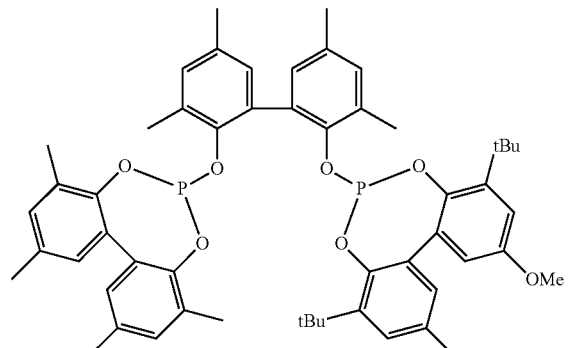

Ligand 1a

A) Pyridine and Derivatives

TABLE 3

| Base equivalents | Base | Proportion of 1a in [% by mass] | Proportion of 2a in [% by mass] | Yield in [%] | |
|---|---|---|---|---|---|
| 4 | pyridine | 72.0 | 28.0 | 81 | * |
| 4 | pyridine | 74.0 | 26.0 | 81 | |
| 3 | pyridine | 80.6 | 19.4 | 80 | |
| 2.5 | pyridine | 81.9 | 18.1 | 78 | |
| 2 | pyridine | 84.2 | 15.8 | 78 | |
| 1.7 | pyridine | 84.2 | 15.8 | 88 | |
| 1.5 | pyridine | 86.3 | 13.7 | 79 | |
| 1.5 | pyridine | 84.5 | 15.5 | 82 | ** |
| 2.5 | pyridine | 81.8 | 18.2 | 78 | *** |
| 2.5 | pyridine | 86.8 | 13.2 | 81 | **** |
| 2.5 | DMAP | 46.6 | 53.4 | 51 | |
| 2 | DMAP | 42.7 | 57.3 | 50 | # |
| 2 | DMAP | 47.8 | 52.2 | 89 | ## |
| 2 | DMAP | 65.1 | 34.9 | 90 | ### |
| 2 | 2-picoline | 76.0 | 24.0 | 67 | |

DMAP = dimethylaminopyridine
*: experiment at 0° C.
**: experiment at 50° C.
***: extended reaction time (5 days)
****: immediate addition rather than gradual dropwise addition
: reaction at 0° C.
: reaction at 3-7° C.
: reaction at 45° C.

As is clearly apparent in Table 3, it is possible to control the isomer distribution of the two constitutional isomers (1a) and (2a) through the choice of base or the corresponding amount of base. For example, it is possible to obtain a 1:1 mixture of the two isomers (1a) and (2a) through use of DMAP as a base at lower temperatures.

B) Various Alkylamines

TABLE 4

| Base equivalents | Base | Proportion of 1a in [% by mass] | Proportion of 2a in [% by mass] | Yield in [%] |
|---|---|---|---|---|
| 2.2 | NEt₃ | 95.4 | 4.6 | 86 |
| 2.3 | DMAB | 97.4 | 2.6 | 86 |
| 2.2 | tributylamine | 94.4 | 5.6 | 90 |
| 2 | tripentylamine | 96.0 | 4.0 | n.d. |
| 2 | trihexylamine | 97.8 | 2.2 | 94 |

NEt₃: triethylamine
DMAB: dimethylaminobutane
n.d.: not determined

As is clearly apparent in Table 4, it is possible through the selection of trialkylamines as base to obtain an isomer mixture in which the unsymmetric isomer (1a) is present with a purity of >90% as the main component and the symmetric isomer (2a) constitutes the corresponding secondary component.

C) Various Base Mixtures

TABLE 5

| Bases | Ratio | Proportion of 1a in [% by mass] | Proportion of 2a in [% by mass] | Yield in [%] |
|---|---|---|---|---|
| pyr/NEt₃ | 4:1 | 78.2 | 21.8 | 56 |
| pyr/NEt₃ | 4:0.5 | 59.6 | 40.4 | 87 |
| pyr/NEt₃ | 4:0.25 | 59.7 | 40.3 | 80 |
| pyr/NEt₃ | 3:0.5 | 62.4 | 37.6 | 81 |
| pyr/NEt₃ | 2:0.5 | 69.1 | 30.9 | 84 |
| pyr/NBu₃ | 2:0.5 | 72.4 | 27.6 | 78 |
| pyr/NBu₃ | 2:0.25 | 47.9 | 52.1 | 81 |
| pyr/NBu₃ | 2:2 | 91.8 | 8.2 | 83 |
| pyr/NBu₃ | 2.5:0.2 | 81.0 | 19.0 | 80 |
| pyr/NBu₃ | 2.5:2 | 92.6 | 7.4 | 69 |

NBu₃: tributylamine
DMAP: dimethylaminopyridine
pyr: pyridine

NBu₃: tributylamine

DMAP: dimethylaminopyridine pyr: pyridine

As is clearly apparent in Table 5, it is possible to control the isomer distribution of the two constitutional isomers (1a) and (2a) through the use of base mixtures and the corresponding amount of base therein.

It is thus possible to influence the isomer distribution of the two constitutional isomers (1a) and (2a) through the selection of the base or base mixture used, such that one isomer is present as the main component. Through the selection of trialkylamines as the base, it is possible to obtain an isomer mixture in which the unsymmetric isomer (1a) is present with a purity of >90% as the main component and the symmetric isomer (2a) constitutes the corresponding secondary component. Since this mixture also shows very good overall performance in the hydroformylation, it is possible to dispense with further purification steps.

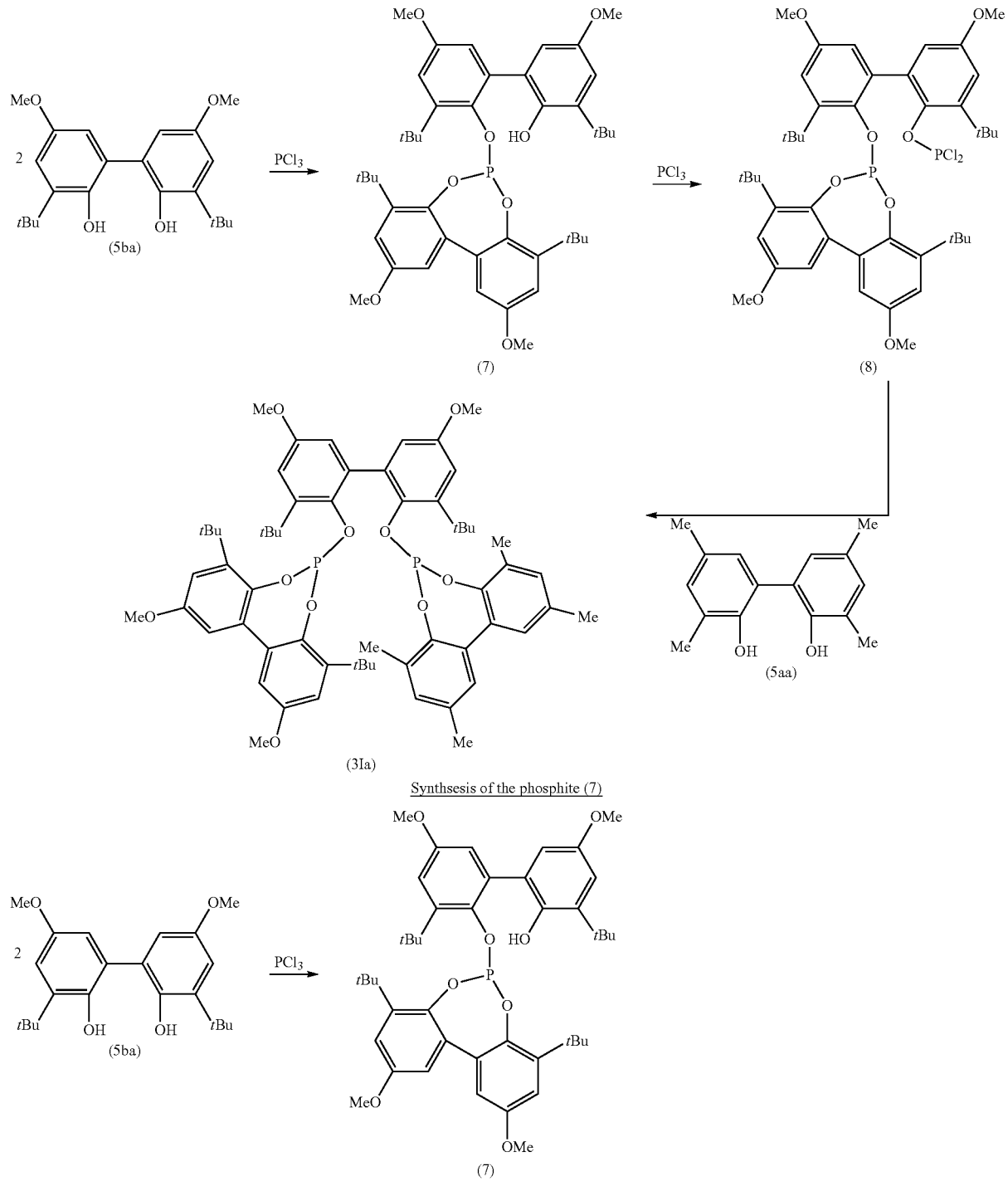

A secured 1000 ml Schlenk is initially charged with 400 ml of dried toluene, 8.9 ml (0.1 mol) of phosphorus trichloride are added by means of a syringe and the mixture is cooled to 0° C.

71.6 g (0.2 mol) of 3,3'-di-tert-butyl-2,2'-dihydroxy-5,5'-dimethoxybiphenyl are weighed into a 500 ml Schlenk and dissolved in 325 ml of dried toluene and 49 ml (0.35 mol) of dried triethylamine.

Then the biphenol/Et$_3$N/toluene suspension is added dropwise within 2.5 h to the PCl$_3$/toluene solution cooled to 0° C. and left to react at RT overnight.

The next morning, the solids formed were filtered off and washed repeatedly with dried toluene, and the filtrate was concentrated to dryness. In order to obtain a white solid, ACN was used for further washes. The target product was thus obtained in 79.5% yield (59.1 g).

Synthesis of the diorganophosphite dichlorophosphite (8)

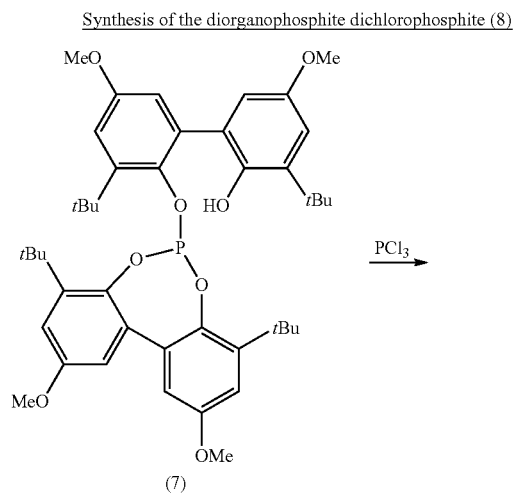

42 g (0.056 mol) of the phosphite (7) were weighed into a secured 250 ml Schlenk, and 275 ml of dried toluene and 17 ml (0.168 mol) of dried triethylamine were added while stirring.

A second 1000 ml Schlenk was first initially charged with 200 ml of dried toluene and then 14.76 ml (0.169 mol) of phosphorus trichloride were added. Subsequently, while stirring vigorously, the above-prepared phosphite/amine/toluene solution was added dropwise to the phosphorus trichloride/toluene solution at RT within 30 minutes. On completion of addition, the reaction mixture was heated to 80° C. for 6 h and allowed to come to RT overnight.

The next morning, the mixture was filtered, the solids were washed with 50 ml of dried toluene, and the filtrate was concentrated to dryness. The product was obtained in 89% yield (45.6 g).

Inventive synthesis of the ligand (3Ia)

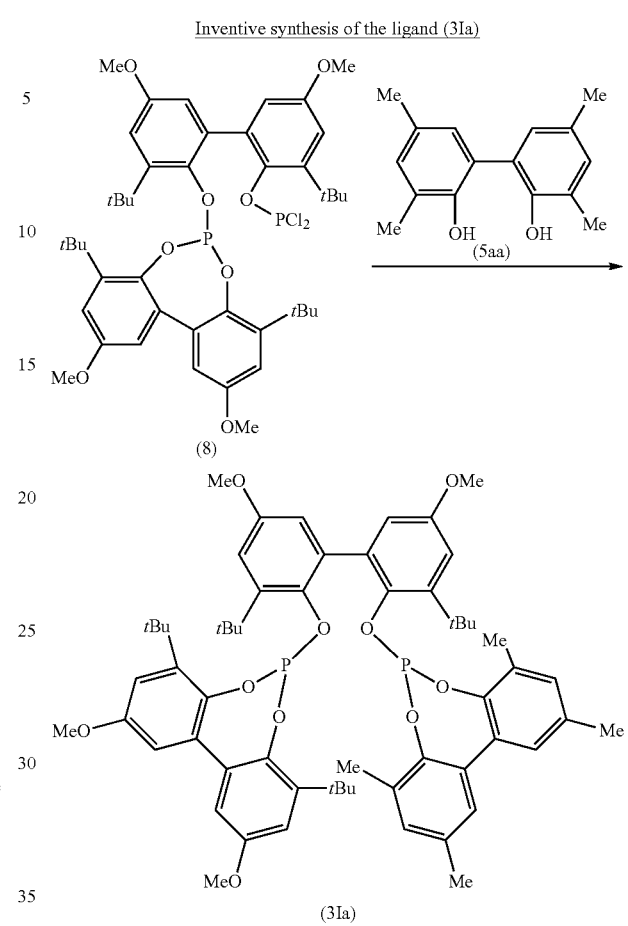

In a glovebox, 3.08 g (0.0036 mol) of diorganophosphite dichlorophosphite (8) were weighed into a secured 100 ml Schlenk and then dissolved in 35 ml of dried toluene.

In a second secured 250 ml Schlenk, 0.872 g (0.0036 mol) of 2,2'-bis(3,5-dimethylphenol) and 1.09 g (0.01 mol) of dried triethylamine were dissolved in 35 ml of toluene.

Then the diorganophosphite dichlorophosphite (8) was slowly and continuously added dropwise at RT to the biphenyl-triethylamine solution with vigorous stirring. Subsequently, the reaction mixture was stirred overnight.

For workup, the solids formed were filtered the next morning and washed twice with 5 ml of dried toluene. The resulting filtrate was then concentrated to dryness. The target product was obtained as a white solid (2.59 g; 71%).

Inventive synthesis of the ligand (4IIa) - general reaction equation

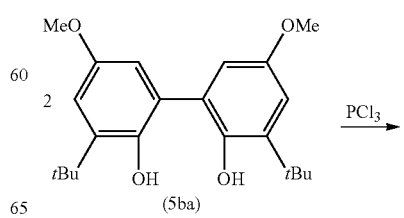

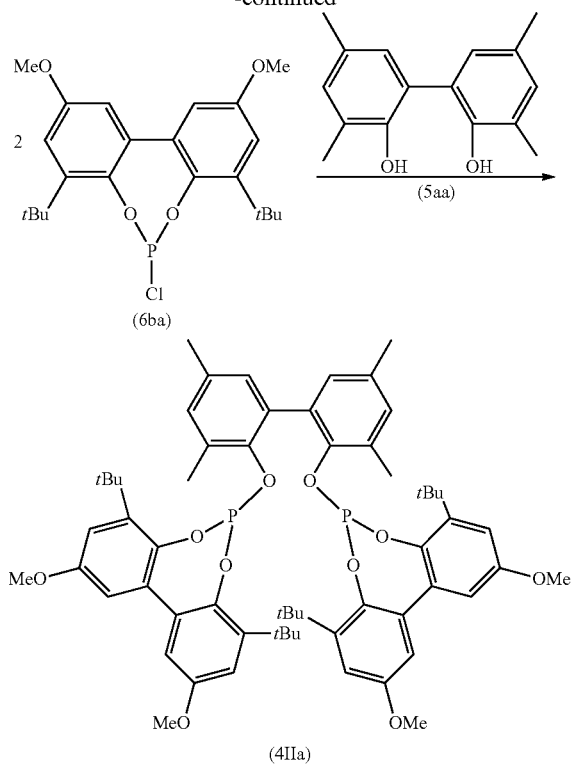

(4IIa)

Preparation of the 3,3'-tert-butyl-2,2'-dihydroxy-5,5'-dimethoxybiphenyl chlorophosphite (6ba)

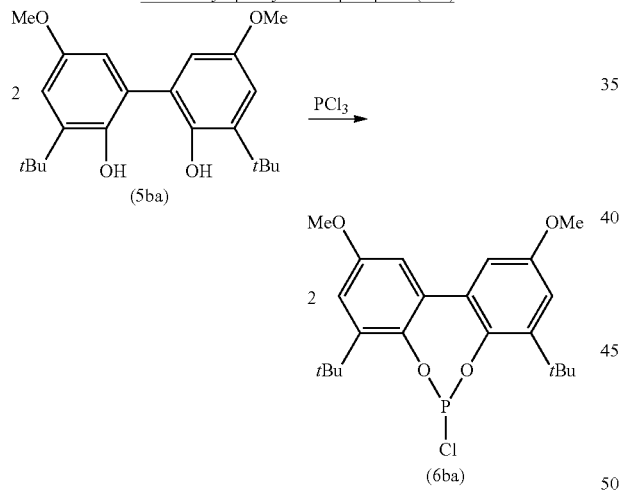

35.8 g (0.1 mol) of 3,3'-tert-butyl-2,2'-dihydroxy-5,5'-dimethoxybiphenol were weighed into a 500 ml Schlenk, and the biphenol was dissolved in 42.3 ml (0.3 mol) of degassed triethylamine and 250 ml of dried toluene.

A second secured 1 L Schlenk was initially charged with 8.8 ml (0.1 mol) of $PCl_3$ in 300 ml of dried toluene and cooled to 0° C. The above-prepared phenol/amine solution was then cautiously added dropwise to this $PCl_3$/toluene solution while stirring vigorously.

After the dropwise addition, the solution was warmed to RT overnight. The next morning, the solids formed were filtered off and the solvent was concentrated to dryness. The product was obtained as a honey-like residue in 56% yield (27.5 g).

Inventive synthesis of the ligand (4IIa)

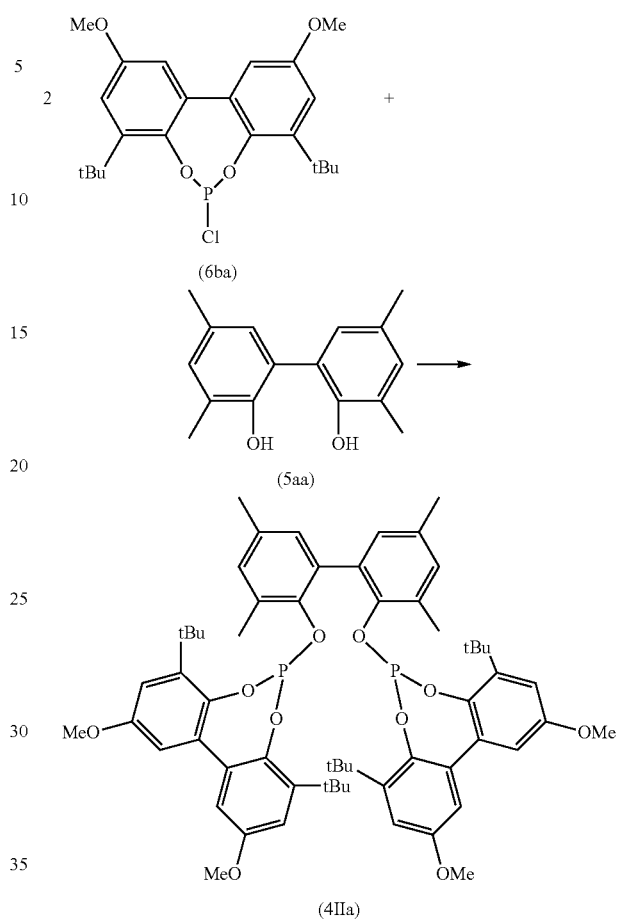

9.79 g (0.022 mol) of chlorophosphite (6ba) were weighed into a secured 250 ml Schlenk and then dissolved in 75 ml of dried toluene.

2.66 g (0.011 mol) of 2,2'-bis(3,5-dimethylphenol) and 2.46 g (0.022 mol) of potassium tert-butoxide were weighed into a further secured 100 ml Schlenk and dissolved in 70 ml of dried toluene while stirring.

At RT, the biphenol/potassium tert-butoxide mixture was slowly and constantly added dropwise at RT to the initially charged chlorophosphite solution while stirring. Subsequently, the mixture was filtered through Celite. The solution was concentrated and the remaining residue was washed with 50 ml of dried acetonitrile. The target product was obtained in 25.5% yield (2.76 g).

Procedure for the Hydroformylation Experiments

Experiment Description—General

The experiments were conducted in 100 ml autoclaves from Parr Instruments. The autoclaves are equipped with an electric heater. The pressure is kept constant by means of mass flow meters and pressure regulators. During the experiment duration, a syringe pump can be used to inject an exactly defined amount of reactant under reaction conditions. Capillary lines and HPLC valves can be used to take samples during the experiment duration, and these can be analysed both by means of GC analysis and by means of LC-MS analysis.

Inventive Results of the Testing of the Various Compound Mixtures of Ligands (1Ia) and (2IIa) in the hydroformylation[a]

TABLE 6

| No. | Ligand | Content of ligand in [%] | Pentanal selectivity in [%][b] | Yield in [%][b] |
|---|---|---|---|---|
| 1 | ligand (1la) | 100 | 94.0 | 92.9 |
| 2* | ligand (1la) + ligand (2lla) | 99.3 + 0.7 | 93.9 | 91.0 |
| 3* | ligand (1la) + ligand (2lla) | 91.9 + 8.1 | 93.7 | 93.1 |
| 4* | ligand (1la) + ligand (2lla) | 90.3 + 9.7 | 93.8 | 92.6 |
| 5* | ligand (1la) + ligand (2lla) | 74 + 26 | 93.7 | 92.7 |
| 6* | ligand (1la) + ligand (2lla) | 80 + 20 | 92.5 | 92.5 |
| 7* | ligand (1la) + ligand (2lla) | 98.7 + 1.3 | 87.9 | 78.7 |

*inventive

[a] conditions: cis-2-butene, Rh(acac)(CO)$_2$ ([Rh]=95 ppm), L/Rh=6:1, 40 ml of toluene, compound 11, 120° C., 20 bar CO/H$_2$ (1:1), 1,2,4,5-tetraisopropylbenzene as internal GC standard. [b] GC analysis with 1,2,4,5-tetraisopropylbenzene as internal GC standard. # further secondary components, including unconverted chlorophosphite, present in relatively large amounts. The desired composition of the two ligands (1Ia) and (2IIa) is present only in a purity of 30% in a mixture with other components/impurities.

In a comparison of the various ligand mixtures of the ligands (1Ia) and (2IIa) (Table 6, entries 2-6) with the hydroformylation result for the pure ligand (1 Ia) (Table 6, entry 1), it is found that the mixtures have very good pentanal selectivities and yields. Even when a ligand mixture in which the ligand (1Ia) is present only in a purity of about 30% (Table 6, entry 7) is used, a very good yield and selectivity were still generated. Through the use of this mixture of bisphosphite compounds, consisting of ligands (1Ia) and (2IIa), the technical object was thus achieved in full, and the corresponding aldehydes were obtained in good to very good yields and selectivities.

It has thus been shown that it is also possible to use ligand mixtures in hydroformylation reactions.

Inventive results of the testing of the various compound mixtures of ligands (1Ia), (3Ia) and (4IIa) in the hydroformylation[a]:

TABLE 7

| No. | Ligands | Content of ligands | Ratio of the ligands in [%][e] | Pentanal selectivity in mol [%][b] | Yield in [%][b] |
|---|---|---|---|---|---|
| 1 | ligand (3la) | 100% | L3la: 100% | 53.2 | 76.2 |
| 2 | ligand (4lla) | 100% | L4la: 100% | 61.8[d] | 76.2 |
| 3* | ligand (3la) + ligand (4lla) | L3la:L4lla:Rh 3.7:0.41:1 | L3la: 90% + L4lla: 10% | 43.9 | 77.2 |
| 4* | ligand (3la) + ligand (4lla) | L3la:L4lla:Rh 2.96:1.07:1 | L3la: 73% + L4lla: 27% | 46.0 | 72.4 |
| 5* | ligand (3la) + ligand (4lla) | L3la:L4lla:Rh 1.8:1.8:1 | L3la: 50% + L4lla: 50% | 42.8 | 74.4 |
| 6* | ligand (3la) + ligand (4lla) | L3la:L4lla:Rh 1.1:3.1:1 | L3la: 26% + L4lla: 74% | 37.1 | 72.2 |
| 7* | ligand (3la) + ligand (4lla) | L3la:L4lla:Rh 0.41:3.55:1 | L3la: 10% + L4lla 90% | 32.7 | 72.4 |

*inventive

[a] conditions: cis-2-butene, Rh(acac)(CO)$_2$, toluene, compound (11), 120° C., 20 bar CO/H$_2$ (1:1), 1,2,4,5-tetraisopropylbenzene or mesitylene as internal GC standard. [b] GC analysis with 1,2,4,5-tetraisopropylbenzene or mesitylene as internal GC standard. [c] Pentanal selectivity and yield in [%]. [d] Aldehyde yield in [%]. [e] Ratio of the two ligands to one another, normalized to 100%.

The pure ligands (3Ia) and (4IIa) (Table 7, entries 1 and 2) show good pentanal selectivities and yields. As well as the pure ligands, however, it is also possible to use various ligand mixtures of the ligands (3Ia) and (4IIa) (Table 7, entries 3-7).

Experiment Description—Extended Experiment

The experiments were conducted in 100 ml autoclaves from Parr Instruments. The autoclaves are equipped with an electric heater. The pressure is kept constant by means of mass flow meters and pressure regulators. During the experiment duration, a syringe pump can be used to inject an exactly defined amount of reactant under reaction conditions. Capillary lines and HPLC valves can be used to take samples during the experiment duration, and these can be analysed both by means of GC analysis and by means of LC-MS analysis.

The Rh precursor (Rh(acac)(CO)$_2$) and the ligand or the ligand mixtures are initially charged in 40 ml of isononyl benzoate in the autoclave. The Rh concentration is 100 ppm based on the overall reaction mixture used. The ligand excess used is 4:1 in molar terms, based on rhodium.

As a stabilizer in a ratio of 2:1 to the ligand, compound (11) is added as the amine. As a GC standard, 0.5 g of 1,2,4,5-tetraisopropylbenzene is added.

Reaction temperature is 120° C. The reaction pressure is 20 bar of synthesis gas (H$_2$:CO=50:50% by volume).

As the olefin, 4 ml of cis-2-butene each time were metered in with the syringe pump at intervals of about 1 day. GC samples were taken after 1, 2, 4 hours and before the next metered addition.

The following ligands were studied with regard to their stability:

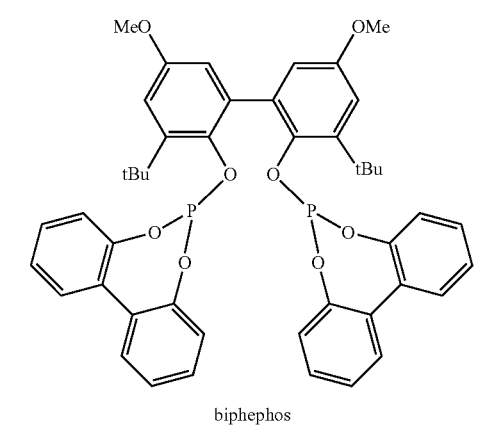

biphephos

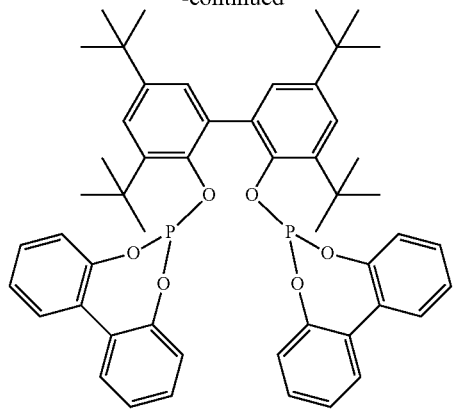

ligand (10IIa)

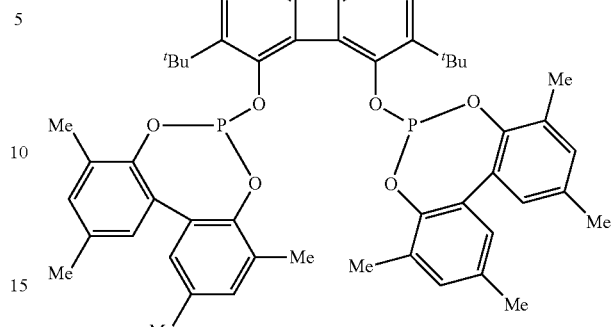

ligand (2IIa)

and a mixture of ligand (10IIa) and ligand (9Ia) ($^{31}$P NMR: L10IIa=75% and L9Ia=25%)

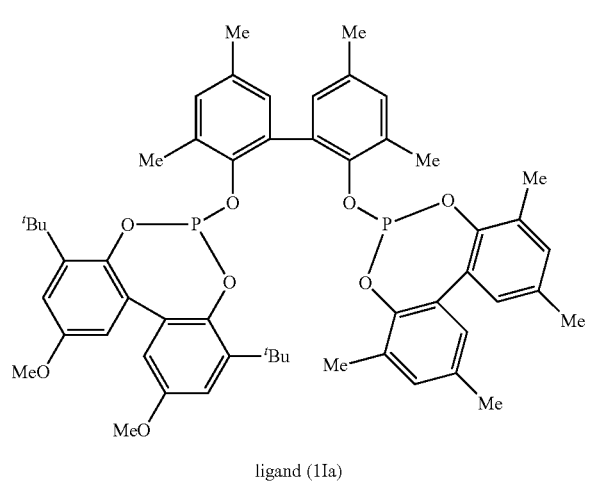

ligand (1Ia)

In addition, mixtures were studied: ligand (1Ia) and ligand (2IIa) ($^{31}$P NMR: L1Ia=91% and L2IIa=9%)

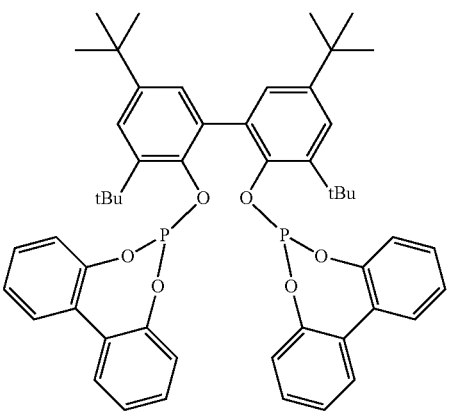

ligand (10IIa)

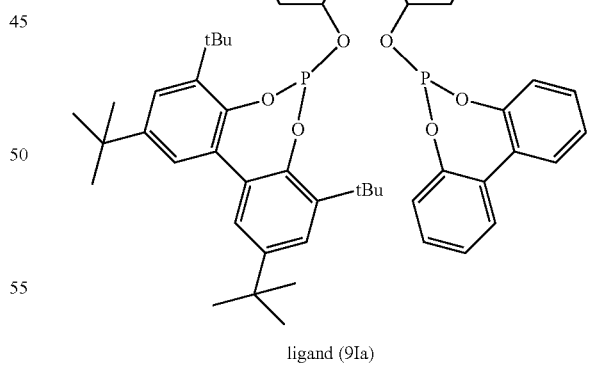

ligand (9Ia)

Results—Extended Experiments

The relative activities are determined by the ratio of 1st order k to k0, i.e. the k value at time 0 in the reaction (start of reaction), and describe the relative decrease in activity during the experiment duration.

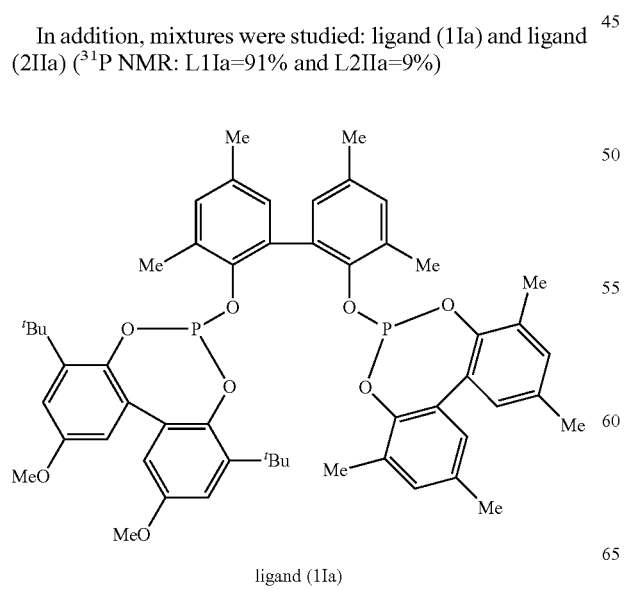

ligand (1Ia)

The 1st order k values are obtained from a plot of (−ln(1−conversion)) against time.

TABLE 8

| Ser. No. | Ligand | Metered addition at run time (h) | 1st order k (min −1) | k/k0 Rel. activity | n/i selectivities |
|---|---|---|---|---|---|
| 1 | biphephos | 0 | 1.39E−02 | 1 | 21 |
| 2 | biphephos | 20.5 | 4.45E−03 | 0.32 | 21 |
| 3 | biphephos | 44.3 | 2.91E−03 | 0.209 | 20 |
| 4 | biphephos | 66.6 | 1.72E−03 | 0.124 | 20 |
| 5 | ligand (10IIa) + ligand (9Ia) | 0 | 1.36E−02 | 1 | 3.1 |
| 6 | ligand (10IIa) + ligand (9Ia) | 20.5 | 5.32E−03 | 0.391 | 2.4 |
| 7 | ligand (10IIa) + ligand (9Ia) | 44.3 | 4.80E−03 | 0.353 | 1.8 |
| 8 | ligand (1Ia) | 0 | 7.74E−03 | 1 | 17 |
| 9 | ligand (1Ia) | 20.8 | 5.10E−03 | 0.659 | 16 |
| 10 | ligand (1Ia) | 44.8 | 3.19E−03 | 0.412 | 15 |
| 11 | ligand (1Ia) | 117.8 | 2.99E−03 | 0.386 | 14 |
| 12* | ligand (1Ia) + ligand (2IIa) | 0 | 1.09E−02 | 1 | 14 |
| 13* | ligand (1Ia) + ligand (2IIa) | 20.8 | 5.65E−03 | 0.518 | 14 |
| 14* | ligand (1Ia) + ligand (2IIa) | 44.8 | 4.13E−03 | 0.379 | 13 |
| 15* | ligand (1Ia) + ligand (2IIa) | 117.8 | 3.35E−03 | 0.307 | 13 |
| 16 | ligand (10IIa) | 0 | 1.72E−02 | 1 | 14 |
| 17 | ligand (10IIa) | 22.4 | 9.00E−03 | 0.523 | 13 |
| 18 | ligand (10IIa) | 44.7 | 5.39E−03 | 0.313 | 13 |
| 19 | ligand (10IIa) | 68.3 | 3.31E−03 | 0.192 | 13 |

*inventive

The decline in catalyst activity with the biphephos ligand and ligand (10IIa) is (Table 8; entries 1-4, 16-19) much more marked than with the ligand (1Ia) (Table 8; entries 8-11). It is remarkable that the relative activity of the ligand (1Ia) after nearly twice the reaction time (Table 8; entry 11) is still more than twice as high as for the other two ligands after half the reaction time (Table 5; entries 4 and 19). In addition, the n/i ratio for the catalyst with the ligand (10IIa) is still very high.

Comparing the mixture of the ligands (1Ia)+(2IIa) with the pure ligand (1Ia) (Table 8; entries 8-11, 12-15), the mixture after a run time of 117 hours shows a comparable activity and selectivity to the pure ligand (1Ia). The mixture of the ligands (10IIa)+(9Ia) from the start shows a much poorer selectivity than the pure ligand (10IIa) and also the mixture of ligand (1Ia)+(2IIa) (Table 8; entries 5-7, 12-15 and 16-19).

The addition of the unsymmetric ligand (9Ia) to the symmetric ligand (10IIa) leads to a drastic collapse in selectivity (Table 8; entries 5-7). This corresponds to the results from the prior art (see in Rhodium-catalyzed Hydroformylation, ed. by P. W. N. M. van Leeuwen and C. Claver, Kluwer Academic Publishers 2006, AA Dordrecht, NL, pages 45-46). In complete contrast to this, the unsymmetric ligand (1Ia), both as a pure substance and in a mixture with the ligand (2IIa) (Table 8; entries 8-11, 12-15), completely surprisingly features excellent service lives and very good selectivities. It has also been shown that mixtures of constitutional ligand compounds (1Ia) and (2IIa) can thus also be used directly from the synthesis without additional complex purification operations.

Inventive Results—Substrate Variation

For the experiments which follow, the following mixture was studied: ligand (1Ia)+ligand (2IIa) ($^{31}$P NMR: LI1a=91%+LI2a=9%).

Example 1

In a 100 ml autoclave from Parr Instruments, 4.8 g of propene were hydroformylated at 120° C. and 30 bar. As the precursor, 0.005 g of Rh(acac)(CO)$_2$ was initially charged in 43.08 g of toluene. As the ligand, 0.0708 g of the above-described ligand mixture ($^{31}$P NMR: LI1a=91%+LI2a=9%) was used in the catalyst mixture solution. 0.0401 g of the compound (11) was added as the organic amine, and 0.5033 g of TIPB as the GC standard. The reactant was metered in after attainment of the reaction temperature envisaged.

During the reaction, the pressure was kept constant via synthesis gas regulation with a mass flow meter. Samples were taken from the reaction mixture after 20 hours. 88.4 mol % butanal, 6.48 mol % 2-methylpropanal and 2.79 mol % propane were formed. The regioselectivity for n-butanal is 93.2%.

Example 2

In a 100 ml autoclave from Parr Instruments, 6.7 g of cis-2-butene were hydroformylated at 120° C. and 20 bar. As the precursor, 0.0053 g of Rh(acac)(CO)$_2$ was initially charged in 43.48 g of toluene. As the ligand, 0.0671 g of the above-described ligand mixture ($^{31}$P NMR: LI1a=91%+LI2a=9%) was used in the catalyst mixture solution. 0.0381 g of the compound (11) was added as the organic amine, and 0.5099 g of TIPB as the GC standard. The reactant was metered in after attainment of the reaction temperature envisaged.

During the reaction, the pressure was kept constant via synthesis gas regulation with a mass flow meter. Samples were taken from the reaction mixture after 20 hours. 84.6 mol % pentanal, 5.70 mol % 2-methylbutanal and 3.43 mol % n-butane were formed. The regioselectivity for n-pentanal is 93.7%.

Example 3

In a 100 ml autoclave from Parr Instruments, 6.7 g of 1-butene were hydroformylated at 120° C. and 20 bar. As the precursor, 0.0052 g of Rh(acac)(CO)$_2$ was initially charged in 43.08 g of toluene. As the ligand, 0.0694 g of the above-described ligand mixture ($^{31}$P NMR: LI1a=91%+LI2a=9%) was used in the catalyst mixture solution. 0.0378 g of the compound (11) was added as the organic amine, and 0.5052 g of TIPB as the GC standard. The reactant was metered in after attainment of the reaction temperature envisaged.

During the reaction, the pressure was kept constant via synthesis gas regulation with a mass flow meter. Samples were taken from the reaction mixture after 20 hours. 86.5 mol % pentanal, 5.08 mol % 2-methylbutanal and 3.23 mol % n-butane were formed. The regioselectivity for n-pentanal is 98.9%.

Example 4

In a 100 ml autoclave from Parr Instruments, 6.7 g of isobutene were hydroformylated at 120° C. and 20 bar. As the precursor, 0.0051 g of Rh(acac)(CO)$_2$ was initially charged in 42.1 g of toluene. As the ligand, 0.0678 g of the above-described ligand mixture ($^{31}$P NMR: LI1a=91%+LI2a=9%) was used in the catalyst mixture solution. 0.0369 g of the compound (11) was added as the organic amine, and 0.4937 g of TIPB as the GC standard. The reactant was metered in after attainment of the reaction temperature envisaged.

During the reaction, the pressure was kept constant via synthesis gas regulation with a mass flow meter. Samples were taken from the reaction mixture after 20 hours. 64.0 mol % 3-methylbutanal, 0.07 mol % pivalaldehyde and 2.92 mol % isobutane were formed.

Example 5

In a 100 ml autoclave from Parr Instruments, 7.4 g of a C-4 mixture having the following composition: 2.9 mol % isobutane, 9.9 mol % n-butane, 28.7 mol % 1-butene, 43.5 mol % isobutene, 14.6 mol % 2-butenes and 0.2 mol % 1,3-butadiene were hydroformylated at 120° C. and 20 bar. As the precursor, 0.0048 g of Rh(acac)(CO)$_2$ was initially charged in 41.49 g of toluene. As the ligand, 0.0681 g of the above-described ligand mixture ($^{31}$P NMR: LI1a=91%+LI2a=9%) was used in the catalyst mixture solution. 0.0367 g of the compound (11) was added as the organic amine, and 0.5027 g of TIPB as the GC standard. The reactant was metered in after attainment of the reaction temperature envisaged.

During the reaction, the pressure was kept constant via synthesis gas regulation with a mass flow meter. Samples were taken from the reaction mixture after 20 hours. The output comprises 32.7% 3-methylbutanal (isobutene conversion 75.2 mol %), 39.44 mol % n-pentanal and 2.18 mol % 2-methylbutanal (butenes conversion 78.1 mol %, regioselectivity for n-pentanal 94.8%). As hydrogenation products, 4.13 mol % isobutane and 9.95 mol % n-butane were found in the output.

Example 6

In a 100 ml autoclave from Parr Instruments, 7.0 g of a C-4 mixture having the following composition: 5.9 mol % isobutane, 15.6 mol % n-butane, 52.9 mol % 1-butene, 0.1 mol % isobutene, 24.8 mol % 2-butenes and 0.5 mol % 1,3-butadiene were hydroformylated at 120° C. and 20 bar. As the precursor, 0.0054 g of Rh(acac)(CO)$_2$ was initially charged in 46.93 g of toluene. As the ligand, 0.0755 g of the above-described ligand mixture ($^{31}$P NMR: LI1a=91%+LI2a=9%) was used in the catalyst mixture solution. 0.0412 g of the compound (11) was added as the organic amine, and 0.5467 g of TIPB as the GC standard. The reactant was metered in after attainment of the reaction temperature envisaged.

During the reaction, the pressure was kept constant via synthesis gas regulation with a mass flow meter. Samples were taken from the reaction mixture after 20 hours. The output comprises 0.17 mol % 3-methylbutanal, 70.31 mol % n-pentanal and 4.20 mol % 2-methylbutanal (butenes conversion 93.4 mol %, regioselectivity for n-pentanal 94.4%). As hydrogenation products, 5.52 mol % isobutane and 18.1 mol % n-butane were found in the output.

Example 7

In a 100 ml autoclave from Parr Instruments, 5.0 g of a C-4 mixture having the following composition: 5.9 mol % isobutane, 22.0 mol % n-butane, 45.5 mol % 1-butene, 2.1 mol % isobutene, 17.1 mol % 2-butenes and 0.2 mol % 1,3-butadiene were hydroformylated at 120° C. and 20 bar. As the precursor, 00044 g of Rh(acac)(CO)$_2$ was initially charged in 37.96 g of toluene. As the ligand, 0.0611 g of the above-described ligand mixture ($^{31}$P NMR: LI1a=91%+LI2a=9%) was used in the catalyst mixture solution. 0.0333 g of the compound (11) was added as the organic amine, and 0.4422 g of TIPB as the GC standard. The reactant was metered in after attainment of the reaction temperature envisaged.

During the reaction, the pressure was kept constant via synthesis gas regulation with a mass flow meter. Samples were taken from the reaction mixture after 20 hours. The output comprises 1.52 mol % 3-methylbutanal (isobutene conversion 72.1 mol %), 63.2 mol % n-pentanal and 3.13 mol % 2-methylbutanal (butenes conversion 95.6 mol %, regioselectivity for n-pentanal 95.3%). As hydrogenation products, 5.41 mol % isobutane and 23.89 mol % n-butane were found in the output.

Example 8

In a 100 ml autoclave from Parr Instruments, 6.4 g of a C-4 mixture having the following composition: 3.4 mol % isobutane, 13.0 mol % n-butane, 47.3 mol % 1-butene, 13.9 mol % isobutene, 21.6 mol % 2-butenes and 0.4 mol % 1,3-butadiene were hydroformylated at 120° C. and 20 bar. As the precursor, 0.0052 g of Rh(acac)(CO)$_2$ was initially charged in 44.95 g of toluene. As the ligand, 0.0704 g of the above-described ligand mixture ($^{31}$P NMR: LI1a=91%+LI2a=9%) was used in the catalyst mixture solution. 0.0387 g of the compound (11) was added as the organic amine, and 0.5318 g of TIPB as the GC standard. The reactant was metered in after attainment of the reaction temperature envisaged.

During the reaction, the pressure was kept constant via synthesis gas regulation with a mass flow meter. Samples were taken from the reaction mixture after 20 hours. The output comprises 9.93 mol % 3-methylbutanal (isobutene conversion 71.7 mol %), 62.6 mol % n-pentanal and 2.98 mol % 2-methylbutanal (butenes conversion 95.6 mol %, regioselectivity for n-pentanal 95.5%).

As hydrogenation products, 3.59 mol % isobutane and 15.41 mol % n-butane were found in the output.

Example 9

In a 100 ml autoclave from Parr Instruments, 6.8 g of a C-4 mixture having the following composition: 0.1 mol % isobutane, 27.6 mol % n-butane, 27.9 mol % 1-butene, 0.1 mol % isobutene and 44.0 mol % 2-butenes were hydroformylated at 120° C. and 20 bar. As the precursor, 0.0051 g of Rh(acac)(CO)$_2$ was initially charged in 42.29 g of toluene. As the ligand, 0.0681 g of the above-described ligand mixture ($^{31}$P NMR: LI1a=91%+LI2a=9%) was used in the catalyst mixture solution. 0.0371 g of the compound (11) was added as the organic amine, and 0.4960 g of TIPB as the GC standard. The reactant was metered in after attainment of the reaction temperature envisaged.

During the reaction, the pressure was kept constant via synthesis gas regulation with a mass flow meter. Samples were taken from the reaction mixture after 20 hours. The output comprises 60.45 mol % n-pentanal and 3.51 mol % 2-methylbutanal (butenes conversion 92.8 mol %, regioselectivity for n-pentanal 94.5%). As hydrogenation products, 0.1 mol % isobutane and 28.8 mol % n-butane were found in the output.

Example 10

In a 100 ml autoclave from Parr Instruments, 6.8 g of a C-4 mixture having the following composition: 63.6 mol % n-butane, 1.0 mol % 1-butene and 35.8 mol % 2-butenes were hydroformylated at 120° C. and 20 bar. As the precursor, 0.0049 g of Rh(acac)(CO)$_2$ was initially charged in 40.42 g of toluene. As the ligand, 0.0651 g of the above-described ligand mixture ($^{31}$P NMR: LI1a=91%+LI2a=9%) was used in the catalyst mixture solution. 0.0354 g of the compound (11) was added as the organic amine, and 0.4740 g of TIPB as the GC standard. The reactant was metered in after attainment of the reaction temperature envisaged.

During the reaction, the pressure was kept constant via synthesis gas regulation with a mass flow meter. Samples were taken from the reaction mixture after 20 hours. The output comprises 27.76 mol % n-pentanal and 2.14 mol % 2-methylbutanal (butenes conversion 81.0 mol %, regioselectivity for n-pentanal 92.8%). As hydrogenation products, 65.0 mol % n-butane was found in the output.

Example 11

In a 100 ml autoclave from Parr Instruments, 6.8 g of trans-2-butene were hydroformylated at 120° C. and 20 bar. As the precursor, 0.0054 g of Rh(acac)(CO)$_2$ was initially charged in 43.78 g of toluene. As the ligand, 0.0696 g of the above-described ligand mixture ($^{31}$P NMR: LI1a=91%+LI2a=9%) was used in the catalyst mixture solution. 0.0370 g of the compound (11) was added as the organic amine, and 0.5121 g of TIPB as the GC standard. The reactant was metered in after attainment of the reaction temperature envisaged.

During the reaction, the pressure was kept constant via synthesis gas regulation with a mass flow meter. Samples were taken from the reaction mixture after 20 hours.

The output comprises 85.4 mol % n-pentanal and 5.95 mol % 2-methylbutanal (regioselectivity for n-pentanal 93.4%). As hydrogenation products, 3.99 mol % n-butane was found in the output.

Example 12

In a 100 ml autoclave from Parr Instruments, 6.0 g of a hydrocarbon mixture from catalytic cracking plants having the following composition: 1.5 mol % propane, 0.8 mol % propene, 28.1 mol % isobutane, 8.1 mol % n-butane, 16.4 mol % 1-butene, 16.9 mol % isobutene, 28.2 mol % 2-butenes, 0.5 mol % 1,3-butadiene and fractions of C5 olefins and hydrocarbons were hydroformylated at 120° C. and 20 bar. As the precursor, 0.0046 g of Rh(acac)(CO)$_2$ was initially charged in 39.43 g of toluene. As the ligand, 0.0672 g of the above-described ligand mixture ($^{31}$P NMR: LI1a=91%+LI2a=9%) was used in the catalyst mixture solution. 0.0331 g of the compound (11) was added as the organic amine, and 0.4665 g of TIPB as the GC standard. The reactant was metered in after attainment of the reaction temperature envisaged. During the reaction, the pressure was kept constant via synthesis gas regulation with a mass flow meter. Samples were taken from the reaction mixture after 20 hours.

The output comprises 1.2 mol % propane, 0.68 mol % butanal, 26.9 mol % isobutane, 9.66 mol % n-butane, 12.66 mol % 3-methylbutanal (74.8% isobutene conversion), 39.5 mol % pentanal, 2.07 mol % 2-methylbutanal (n-butenes conversion 97.9%, regioselectivity for n-pentanal 95.0%).

Example 13

In a 100 ml autoclave from Parr Instruments, 5.8 g of 1,3-butadiene were hydroformylated at 120° C. and 20 bar. As the precursor, 0.0048 g of Rh(acac)(CO)$_2$ was initially charged in 41.19 g of toluene. As the ligand, 0.0677 g of the above-described ligand mixture ($^{31}$P NMR: LI1a=91%+LI2a=9%) was used in the catalyst mixture solution. 0.0364 g of the compound (11) was added as the organic amine, and 0.4991 g of TIPB as the GC standard. The reactant was metered in after attainment of the reaction temperature envisaged. During the reaction, the pressure was kept constant via synthesis gas regulation with a mass flow meter. Samples were taken from the reaction mixture after 20 hours.

The output comprises 0.26 mol % n-butane, 14.25% n-butenes, 16.65% aldehydes and 9.68 mol % 4-vinylcyclohexene. The total conversion of 1,3-butadiene is 42.4%.

Example 14

In a 100 ml autoclave from Parr Instruments, 1.8 g of ethene were hydroformylated at 120° C. and 50 bar. As the precursor, 0.0050 g of Rh(acac)(CO)$_2$ was initially charged in 42.68 g of toluene. As the ligand, 0.0668 g of the above-described ligand mixture ($^{31}$P NMR: LI1a=91%+LI2a=9%) was used in the catalyst mixture solution. 0.0363 g of the compound (11) was added as the organic amine, and 0.5095 g of TIPB as the GC standard. The reactant was metered in after attainment of the reaction temperature envisaged. During the reaction, the pressure was kept constant via synthesis gas regulation with a mass flow meter. Samples were taken from the reaction mixture after 20 hours. The conversion for propanal is 98.7%.

Example 15

In a 100 ml autoclave from Parr Instruments, 5.74 g of methyl oleate were hydroformylated at 120° C. and 20 bar. As the precursor, 0.0049 g of Rh(acac)(CO)$_2$ was initially charged in 42.00 g of toluene. As the ligand, 0.0665 g of the above-described ligand mixture ($^{31}$P NMR: LI1a=91%+LI2a=9%) was used in the catalyst mixture solution. 0.0345 g of the compound (11) was added as the organic amine, and 0.4956 g of TIPB as the GC standard. The reactant was metered in after attainment of the reaction temperature envisaged. During the reaction, the pressure was kept constant via synthesis gas regulation with a mass flow meter. Samples were taken from the reaction mixture after 20 hours. From $^1$H and $^{13}$C NMR spectra, an aldehyde yield of 43.3 mol % was calculated. The regioselectivity for terminal aldehydes is 22.2 mol %. The double bond content is 36.3 mol %.

For the experiments which follow, the ligands (3Ia) and (4IIa) and combinations of (3Ia) and (4IIa) were studied.

Example 16

In a 100 ml autoclave from Parr Instruments, 6.0 g of cis-2-butene were hydroformylated at 120° C. and 20 bar. As the precursor, 0.0049 g of Rh(acac)(CO)$_2$ was initially charged in 44.38 g of toluene. As the ligand, 0.0783 g of ligand (3Ia) was used in the catalyst mixture solution. 0.0392 g of the compound (11) was added as the organic amine, and 0.4981 g of TIPB as the GC standard. The reactant was metered in after attainment of the reaction temperature envisaged.

During the reaction, the pressure was kept constant via synthesis gas regulation with a mass flow meter. Samples were taken from the reaction mixture after 12 hours. 53.2 mol % pentanal, 16.6 mol % 2-methylbutanal and 3.19 mol % n-butane were formed. The regioselectivity for n-pentanal is 76.2%.

Example 17

In a 100 ml autoclave from Parr Instruments, 5.8 g of cis-2-butene were hydroformylated at 120° C. and 20 bar. As the precursor, 0,006 g of Rh(acac)(CO)$_2$ was initially charged in 44.3 g of toluene. As the ligand, 0.0907 g of ligand (4IIa) was used in the catalyst mixture solution. 0.0432 g of the compound (11) was added as the organic amine, and 1.7624 g of mesitylene as the GC standard. The reactant was metered in after attainment of the reaction temperature envisaged. During the reaction, the pressure was kept constant via synthesis gas regulation with a mass flow meter. Samples were taken from the reaction mixture after 12 hours. An aldehyde yield of 61.8 mol % was found. The regioselectivity for n-pentanal is 76.2 mol %. The proportion of n-butane is 3.2%.

Example 18

In a 100 ml autoclave from Parr Instruments, 6.4 g of cis-2-butene were hydroformylated at 120° C. and 20 bar. As the precursor, 0.0047 g of Rh(acac)(CO)$_2$ was initially charged in 41.71 g of toluene. As ligands, 0.0674 g of ligand (3Ia) and 0.0075 g of ligand (4IIa) (molar L3Ia:L4IIa:Rh ratio=3.7:0.41:1) were used in the catalyst mixture solution. 0.0346 g of the compound (11) was added as the organic amine, and 1.8862 g of mesitylene as the GC standard. The reactant was metered in after attainment of the reaction temperature envisaged.

During the reaction, the pressure was kept constant via synthesis gas regulation with a mass flow meter. Samples were taken from the reaction mixture after 12 hours. 43.9 mol % pentanal, 13.0 mol % 2-methylbutanal and 2.66 mol % n-butane were formed. The regioselectivity for n-pentanal is 77.2%.

Example 19

In a 100 ml autoclave from Parr Instruments, 6.3 g of cis-2-butene were hydroformylated at 120° C. and 20 bar. As the precursor, 0.0050 g of Rh(acac)(CO)$_2$ was initially charged in 41.17 g of toluene. As ligands, 0.0581 g of ligand (3Ia) and 0.0211 g of ligand (4IIa) (molar L3Ia:L4IIa:Rh ratio=2.96:1.07:1) were used in the catalyst mixture solution. 0.0352 g of the compound (11) was added as the organic amine, and 1.7344 g of mesitylene as the GC standard. The reactant was metered in after attainment of the reaction temperature envisaged.

During the reaction, the pressure was kept constant via synthesis gas regulation with a mass flow meter. Samples were taken from the reaction mixture after 12 hours. 46.0 mol % pentanal, 17.5 mol % 2-methylbutanal and 2.46 mol % n-butane were formed. The regioselectivity for n-pentanal is 72.4%.

Example 20

In a 100 ml autoclave from Parr Instruments, 6.2 g of cis-2-butene were hydroformylated at 120° C. and 20 bar. As the precursor, 0.0055 g of Rh(acac)(CO)$_2$ was initially charged in 43.59 g of toluene. As ligand, 0.0389 g of ligand (3Ia) and 0.0388 g of ligand (4IIa) (molar L3Ia:L4IIa:Rh ratio=1.8:1.8:1) were used in the catalyst mixture solution. 0.0349 g of the compound (11) was added as the organic amine, and 1.8283 g of mesitylene as the GC standard. The reactant was metered in after attainment of the reaction temperature envisaged.

During the reaction, the pressure was kept constant via synthesis gas regulation with a mass flow meter. Samples were taken from the reaction mixture after 12 hours. 42.8 mol % pentanal, 14.8 mol % 2-methylbutanal and 2.11 mol % n-butane were formed. The regioselectivity for n-pentanal is 74.4%.

Example 21

In a 100 ml autoclave from Parr Instruments, 6.3 g of cis-2-butene were hydroformylated at 120° C. and 20 bar. As the precursor, 0.0047 g of Rh(acac)(CO)$_2$ was initially charged in 43.47 g of toluene. As ligand, 0.0203 g of ligand (3Ia) and 0.0576 g of ligand (4IIa) (molar L3Ia:L4IIa:Rh ratio=1.1:3.1:1) were used in the catalyst mixture solution. 0.0362 g of the compound (11) was added as the organic amine, and 1.8681 g of mesitylene as the GC standard. The reactant was metered in after attainment of the reaction temperature envisaged. During the reaction, the pressure was kept constant via synthesis gas regulation with a mass flow meter. Samples were taken from the reaction mixture after 12 hours. 37.1 mol % pentanal, 14.3 mol % 2-methylbutanal and 1.52 mol % n-butane were formed. The regioselectivity for n-pentanal is 72.2%.

Example 22

In a 100 ml autoclave from Parr Instruments, 6.4 g of cis-2-butene were hydroformylated at 120° C. and 20 bar. As the precursor, 0.0050 g of Rh(acac)(CO)$_2$ was initially charged in 43.06 g of toluene. As ligand, 0.0082 g of ligand (3Ia) and 0.0697 g of ligand (4IIa) (molar L3Ia:L4IIa:Rh ratio=0.41:3.55:1) were used in the catalyst mixture solution. 0.0374 g of the compound (11) was added as the organic amine, and 1.7914 g of mesitylene as the GC standard. The reactant was metered in after attainment of the reaction temperature envisaged.

During the reaction, the pressure was kept constant via synthesis gas regulation with a mass flow meter. Samples were taken from the reaction mixture after 12 hours. 32.7 mol % pentanal, 12.5 mol % 2-methylbutanal and 1.12 mol % n-butane were formed. The regioselectivity for n-pentanal is 72.4%.

Examples of Extended Experiments

Example L1

Hydroformylation with the Noninventive Ligand (100) Over 1200 h (Comparative Example 1)

The noninventive ligand of the formula (100) known from EP2280920B1 was used in the hydroformylation of a butene/butane mixture.

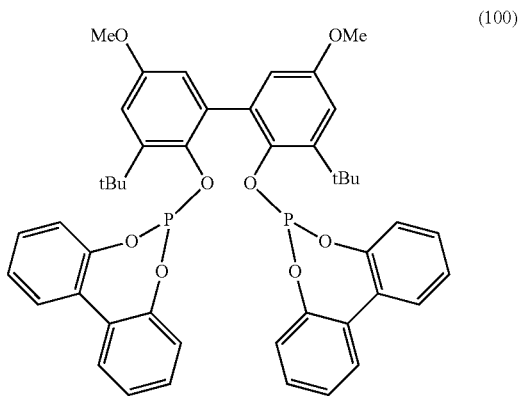 [SMILES: COc1cc(-c2cc(OC)cc(C(C)(C)C)c2Op2oc3ccccc3c3ccccc3o2)c(Op2oc3ccccc3c3ccccc3o2)c(C(C)(C)C)c1]

Ligand (100) was stabilized with the amine of the formula (11).

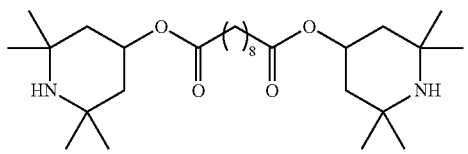
(11)

The continuously operated experiment system consisted essentially of a pressure reactor of capacity 20 liters with a downstream condenser and phase separation vessel (gas/liquid) for the gas phase originating from the reactor, and a cycle gas compressor which returns the gas phase from the phase separation vessel back down into the reaction zone. A portion of this cycle gas is run out of the reaction system as offgas after the phase separation. In order to achieve optimal gas distribution in the reactor system, a gas distributor ring with bores was installed here. By means of installed heating and cooling apparatuses, the temperature of the reactor could be controlled.

Prior to the hydroformylation, the system was purged with nitrogen to free it of oxygen.

Subsequently, the reactor was charged with 12 liters of catalyst solution.

This catalyst solution was composed of 12 kg of a eutectic mixture of biphenyl and diphenyl ether (Diphyl®, heat carrier oil from Lanxess), 3 g of Rh(acac)(CO)2, 36 g of bisphosphite ligand of the formula (100), 67.5 g of amine of the formula (11), and was mixed beforehand in a vessel. The eutectic mixture of biphenyl and diphenyl ether (Diphyl®) was stripped with nitrogen beforehand, in order to remove oxygen and water from the heat carrier oil.

Subsequently, the reactor system was purged with synthesis gas to free it of nitrogen. Once the nitrogen content had fallen below 10% by volume, the reactor system was pressurized to 1.0 MPa with synthesis gas and then heated to 120° C. On attainment of the operating temperature, the reactor system was brought to reaction pressure 1.7 MPa with synthesis gas.

Then the addition of the starting materials was commenced. For this purpose, an input mixture was run through a vaporizer in order to run it into the cycle gas in gaseous form. The input mixture was a mixture of 35% by weight of 2-butenes and 1-butene in a concentration of about 1%. The rest was n-butane.

The following throughputs were set: 0.3 kg/h of input mixture, 75 l (STP)/h of synthesis gas (50% by vol. of H2 and 50% by vol. of CO).

For the daily metered addition of the bisphosphite ligand (100) and amine (11), a 1.4% solution of the bisphosphite ligand (100) in n-pentanal, which had been freed of residual C4 hydrocarbons (<3%) beforehand by stripping with nitrogen, was made up. The amine (11) was used in a threefold molar excess relative to the bisphosphite ligand (100). For better stabilization of this solution, the amine (11) was added to the solution before the bisphosphite ligand (100).

After about 1000 h, a steady state was attained. The reaction products were removed continuously from the reactor via the cycle gas stream and partially condensed out in a condenser at 50° C. The condensed phase was run continuously out of the phase separation vessel. To determine the conversion, samples were taken from the cycle gas upstream and downstream of the reactor.

By a daily metered addition of the above-described ligand solution, it was possible to keep the conversion and regioselectivity constant.

To determine the reactor contents, samples were taken from the reactor and analysed by means of liquid chromatography (HPLC). Under the selected reaction conditions, butene conversions of around 65 to 70% were achieved. The percentage distribution between n-pentanal and 2-methylbutanal, i.e. n/iso selectivity, was 95% to 5%. In the steady-state phase of the experiment, no rhodium degradation was recorded.

Figure 2:
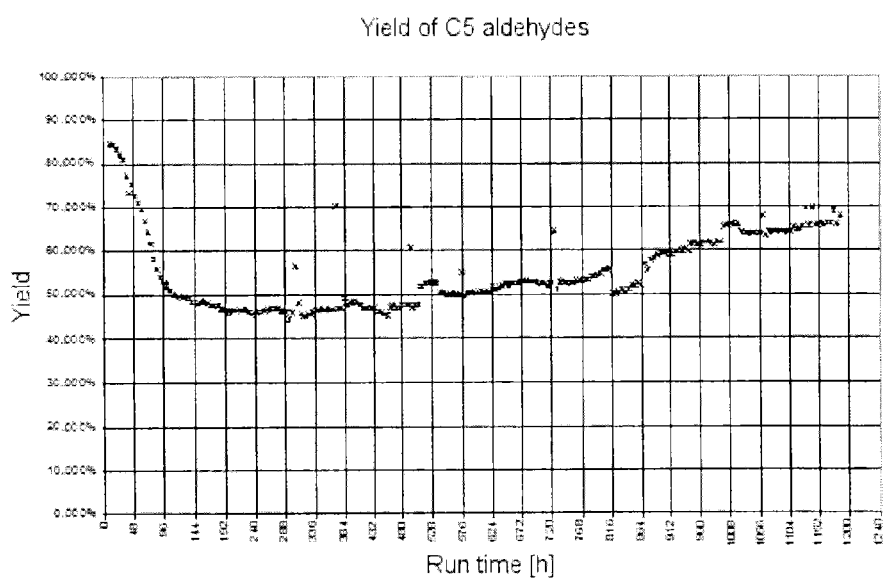
FIG. 2 shows a yield of the C5 aldehydes over the experiment duration in Example L1

The yield of the C5 aldehydes over the experiment duration is plotted in FIG. 2.

FIG. 2: Pentanal yield for Example L1

After 1200 h, the reactor was decompressed and the catalyst solution was analysed. A precipitate was found in the reactor. An analysis of this precipitate showed that it consisted of phosphorus-containing conversion products of the bisphosphite ligand (100) and the amine (11) used. No caking of these precipitated solids whatsoever was found in the reactor.

After removing the precipitate, a portion of the reactor contents was concentrated at 1.2 kPa abs. and bottom temperature 220° C. to 13% based on the starting material. The residue obtained from the liquid was still free-flowing, and no precipitate was found. A rhodium analysis showed that all the rhodium from the starting material was present in this liquid residue.

Example L2

Hydroformylation with the Noninventive Ligand (100) Over 8000 h (Comparative Example 2)

The experiment was performed in the experiment system described in Example L1. The preparation for the experiment and the procedure were analogous to Example L1.

In this example, the catalyst solution was composed of 12 kg of isononyl benzoate, 4.5 g of Rh(acac)(CO)2, 55 g of bisphosphite ligand of the formula (100), 67.5 g of amine of the formula (11). The isononyl benzoate was likewise stripped beforehand with nitrogen, in order to remove oxygen and water from the system.

Subsequently, the reactor system was purged with synthesis gas to free it of nitrogen. Once the nitrogen content had fallen below 10% by volume, the reactor system was pressurized to 1.0 MPa with synthesis gas and then heated to 120° C. On attainment of the operating temperature, the reactor system was brought to reaction pressure 1.7 MPa with synthesis gas.

Subsequently, the addition of the starting materials was commenced. For this purpose, an input mixture was run through a vaporizer in order to run it into the cycle gas in gaseous form. The input mixture was a mixture of 35% by weight of 2-butenes and 1-butene in a concentration of about 1%. The rest was n-butane. The following throughputs were set: 0.3 kg/h of input mixture, 75 l (STP)/h of synthesis gas (50% by vol. of H2 and 50% by vol. of CO).

For the daily metered addition of the bisphosphite ligand (100) and amine (11), a 1.4% solution of the bisphosphite ligand (100) in n-pentanal, which had been freed of residual C4 hydrocarbons (<3%) beforehand by stripping with nitrogen, was made up. The amine (11) was used in a threefold molar excess relative to the bisphosphite ligand (100). For better stabilization of this solution, the amine (11) was added to the solution before the bisphosphite ligand (100).

As in Example L1, a steady state was attained after about 1000 h. The reaction products were removed continuously from the reactor via the cycle gas stream and partially condensed out in a condenser at 50° C. The condensed phase was run continuously out of the phase separation vessel. To determine the conversion, samples were taken from the cycle gas upstream and downstream of the reactor.

By a daily metered addition of the above-described ligand solution, it was possible to keep the conversion and regioselectivity constant.

To determine the reactor contents, samples were taken from the reactor and analysed by means of liquid chromatography (HPLC). Under the selected reaction conditions, butene conversions of around 65 to 70% were achieved. The percentage distribution between n-pentanal and 2-methylbutanal, i.e. n/iso selectivity, was 95% to 5%. In the steady-state phase of the experiment, no rhodium degradation was recorded.

Figure 3:
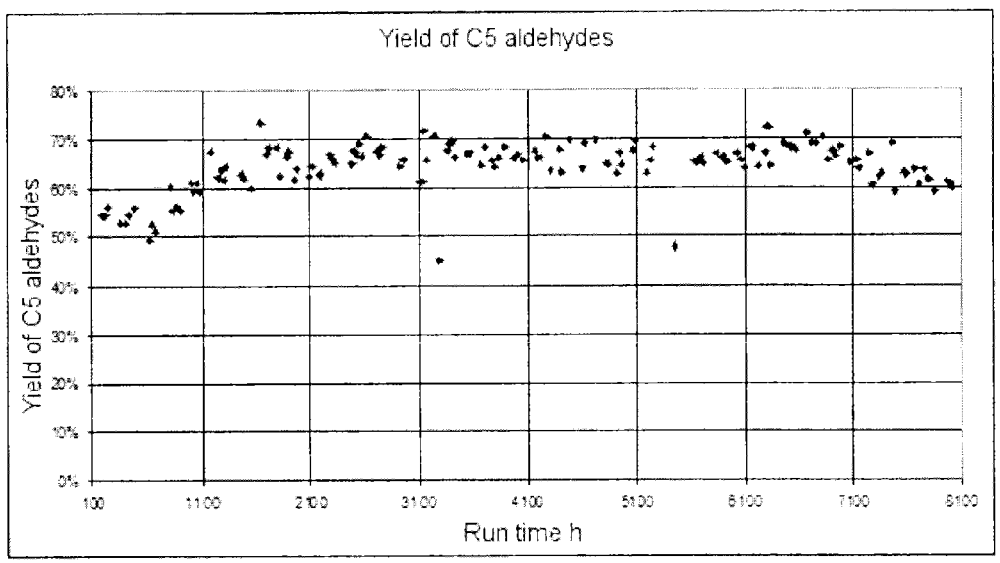
FIG. 3 shows a yield of the C5 aldehydes over the experiment duration in Example L2.

The yield of the C5 aldehydes over the experiment duration is plotted in FIG. 3.

FIG. 3: Pentanal yield for Example L2

After 1500 h, the first precipitates were found in the samples from the reactor. The analysis of these precipitates showed that, just as in Example L1, they consisted of phosphorus-containing conversion products of the bisphosphite ligand (100) and the amine (11) used.

The reaction was conducted for a total of 8100 h; the rhodium losses through sampling were compensated for by addition of corresponding amounts of Rh(acac)(CO)2 to the daily ligand metering solution.

As the reaction proceeded, after about 7000 h, a decline in activity was observed in the reaction and the reaction solution had a tendency to foam. It was no longer possible to operate the process, and the experiment had to be ended.

After the end of the reaction, the reactor was decompressed and the reaction mixture was analysed. Large amounts of solids were found. 250 ml of the reaction solution were stirred under an N2 atmosphere at 40° C. for 4 h, and then the viscosity of the residue was measured. The viscosity was 300 mPas.

Example L3

Hydroformylation with Inventive Catalyst System

The same experiment system was used as in Example L2. The same input mixture and the same synthesis gas were used. The ligand used, however, was a mixture of the two bisphosphite ligands (1Ia) and (2IIa). The ligand of the formula (100) known from EP2280920B1 was not present in the reaction mixture. The same amine (11) as in Comparative Example 1 (L1) was used as a stabilizer. The solvent used was isononyl benzoate.

Prior to the hydroformylation, the system was purged with nitrogen to free it of oxygen.

Subsequently, the reactor was charged with 12 liters of catalyst solution.

This catalyst solution was composed of 12 kg of isononyl benzoate, 4.5 g of Rh(acac)(CO)2, 63 g of ligand isomer mixture of the formulae (1Ia) and (2IIa), 200 g of amine of the formula (11), and was mixed beforehand in a vessel. The isononyl benzoate was stripped beforehand with nitrogen, in order to remove oxygen and water from the solvent.

Subsequently, the reactor system was purged with synthesis gas to free it of nitrogen. Once the nitrogen content had fallen below 10% by volume, the reactor system was pressurized to 1.0 MPa with synthesis gas and then heated to 120° C.

On attainment of the operating temperature, the reactor system was brought to reaction pressure 1.7 MPa with synthesis gas.

Then the addition of the starting materials was commenced. The input mixture was run through a vaporizer in order to run it into the cycle gas in gaseous form. The following throughputs were set: 0.3 kg/h of input mixture, 75 l (STP)/h of synthesis gas.

For the daily metered addition of the isomer mixture consisting of (1Ia) and (2IIa) and amine (11), a 1.4% solution of the ligand mixtures of the bisphosphite ligands (1Ia) and (2IIa) in n-pentanal, which had been freed of residual C4 hydrocarbons (<3%) beforehand by stripping with nitrogen, was made up. The amine (11) was used in a threefold molar excess relative to the ligand isomer mixture consisting of (1Ia) and (2IIa). For better stabilization of this solution, the amine (11) was added to the solution before the bisphosphite ligand isomer mixture.

The reaction products were removed continuously from the reactor via the cycle gas stream and partially condensed out in a condenser at 50° C. The condensed phase was run continuously out of the phase separation vessel. To determine the yield, samples were taken from the cycle gas upstream and downstream of the reactor and analysed by means of a gas chromatograph.

By a daily metered addition of the above-described ligand solution, it was possible to keep the conversion and regioselectivity constant. To determine the reactor contents, samples were taken from the reactor and analysed by means of liquid chromatography (HPLC).

Under the selected reaction conditions, an aldehyde yield between 80% and 90% was established at the start of the reaction. After an operating time of 8000 h, the yield fell to about 65%, caused by the rhodium losses resulting from the sampling. In this case, no foaming of the reaction solution was detectable. The percentage distribution between n-pentanal and 2-methylbutanal, i.e. the regioselectivity, was 92% to 8%.

Figure 4:
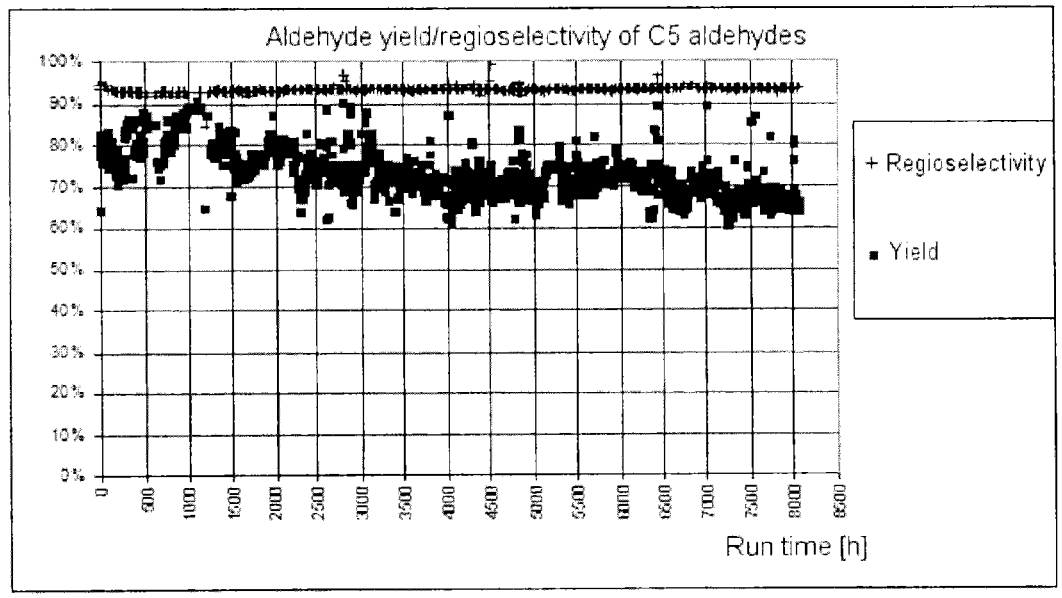
FIG. 4 shows an aldehyde yield and regioselectivity over the experiment duration in Example L3.

Aldehyde yield and regioselectivity are plotted over the experiment duration in FIG. 4.

FIG. 4: Aldehyde yield and regioselectivity for Example L3

In the steady-state phase of the experiment, apart from the rhodium losses resulting from the sampling, no further rhodium degradation was recorded.

Figure 5:
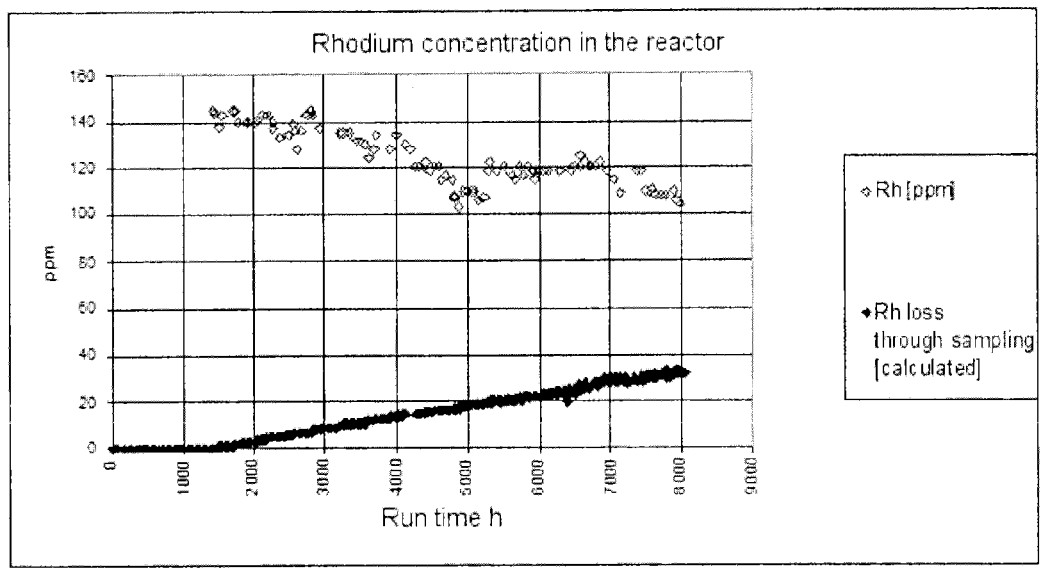
FIG. 5 shows a rhodium concentration in the reactor over the experiment duration in Example L3.

The rhodium concentration in the reactor over the experiment duration is plotted in FIG. 5.

FIG. 5: Rh concentration for Example L3

After the end of the reaction, the reactor was decompressed and the reaction mixture was analysed. No solids were found. 250 ml of the reaction solution were stirred under an N2 atmosphere at 40° C. for 4 h, and then the viscosity of the residue was measured. The viscosity was 20 mPas.

Comparison of Examples L1, L2 and L3

Comparing the corresponding examples, Example L3 which was conducted in accordance with the invention is clearly set apart from Examples L1 and L2, which represent the prior art, by the following features:

Inventive Example L3 does not exhibit any run-in phase, meaning that the system does not show any decline in activity in the first 1000 h of operating time, and hence the plant in Inventive Example L3 produces much more product in the same period.

In Comparative Example 2 (L2), solids occur in the course of the reaction, which can be removed only via an inconvenient filtration. Inventive Example L3 shows no occurrence of solids even after 8000 h, and so it is possible to dispense with the filtration in this process.

Comparative Example 2 (L2) shows distinct foaming of the reaction solution at the end of the experiment, such that the process can no longer be operated. Such behaviour could only be prevented by inconvenient foam breakers. The process according to the invention does not need these aids.

The invention claimed is:

1. A mixture comprising the compounds (Ia) and (IIa):

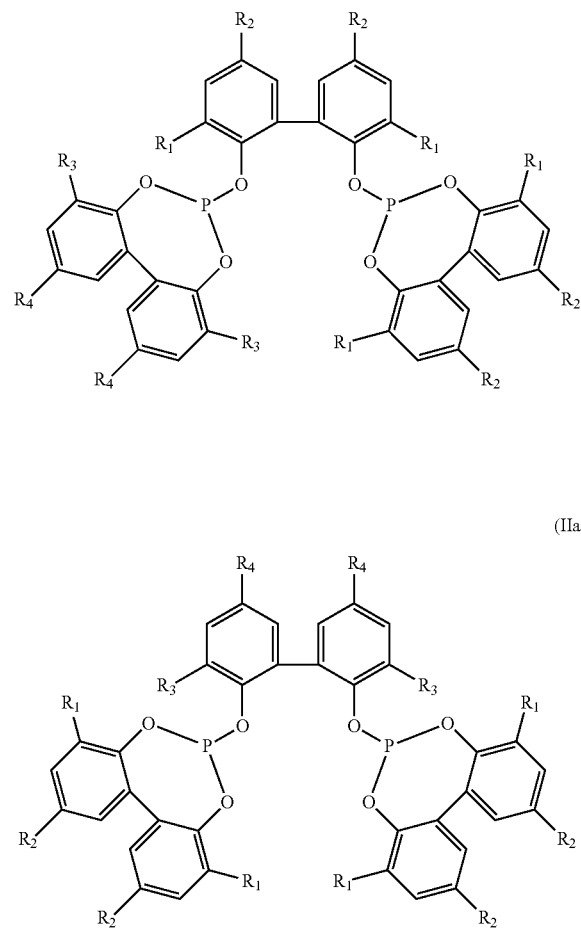

where
R1 is selected from -Me, -tBu, —OMe;
R2 is selected from -Me, -tBu, —OMe;
R3 is selected from -Me, -tBu, —OMe;
R4 is selected from -Me, -tBu, —OMe;
with the proviso that,
if R1 is the same as R3, R2 is not the same as R4,
if R2 is the same as R4, R1 is not the same as R3,
and P can enter into further bonds.

2. The mixture according to claim 1, wherein the content of compound (Ia) ranges from 99.5 to 0.5% by mass, and the content of compound (IIa) ranges from 0.5 to 99.5% by mass.

3. The mixture according to claim 1, comprising the compounds (Ib) and (IIb):

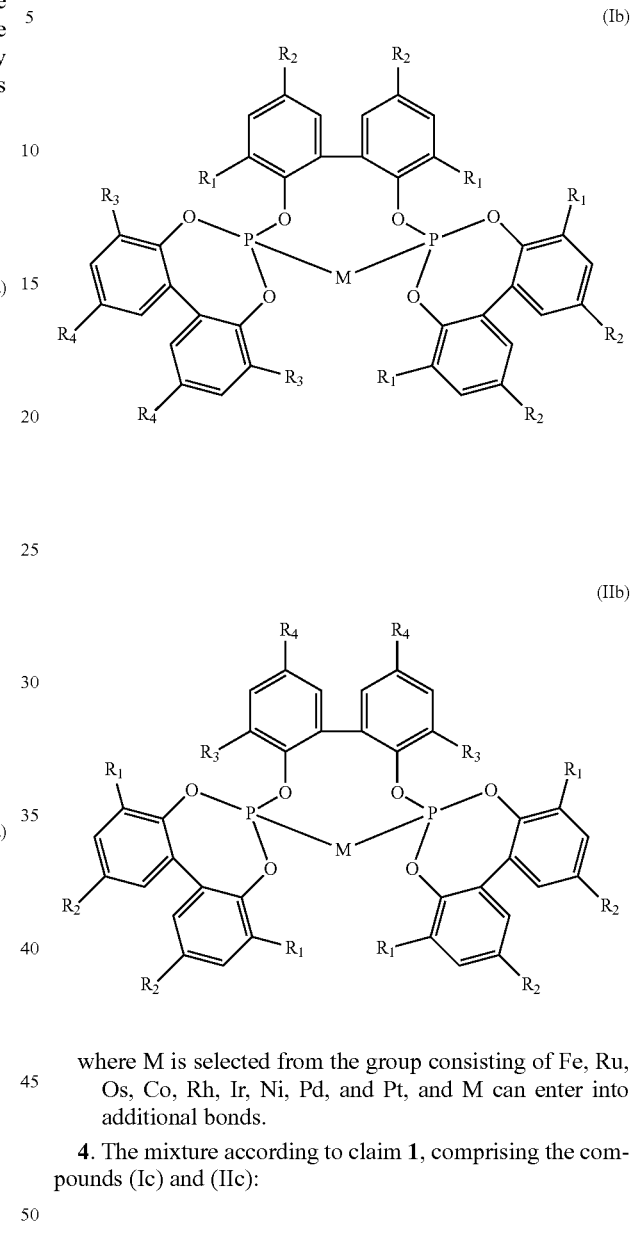

where M is selected from the group consisting of Fe, Ru, Os, Co, Rh, Ir, Ni, Pd, and Pt, and M can enter into additional bonds.

4. The mixture according to claim 1, comprising the compounds (Ic) and (IIc):

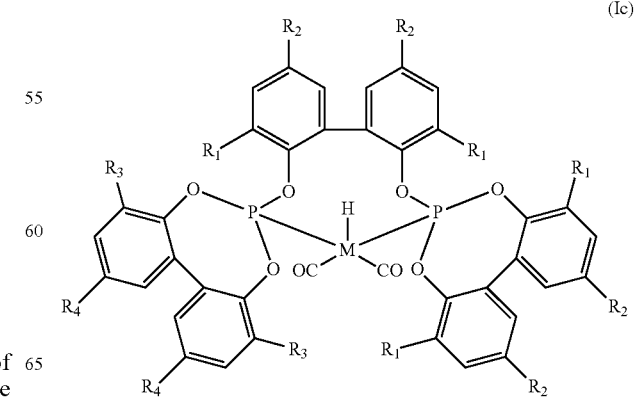

-continued

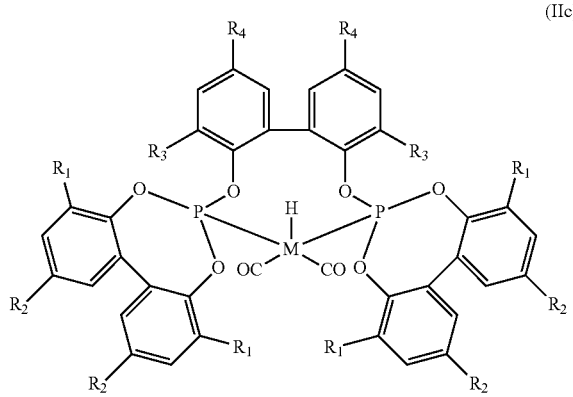

(IIc)

where M is selected from Fe, Ru, Os, Co, Rh, Ir, Ni, Pd, Pt.

5. The mixture according to claim 4, which additionally comprises at least one compound (Ia) or (IIa) not bonded to M.

6. The mixture according to claim 4, where M is Rh.

7. The mixture according to claim 1, where R1 is -Me, and R3 is not -Me.

8. The mixture according to claim 1, where R2 is -Me, and R4 is not -Me.

9. The mixture according to claim 1, where R1 and R2 are each -Me.

10. The mixture according to claim 1, where R1 is -tBu, and R3 is not -tBu.

11. The mixture according to claim 1, where R2 is —OMe, and R4 is not —OMe.

12. A composition comprising:
a mixture according to claim 1,
a further component selected from the group consisting of: bases, organic amines, epoxides, buffer solutions, and ion exchangers.

13. The composition according to claim 12, wherein the organic amine has at least one 2,2,6,6-tetramethylpiperidine unit.

14. A process for preparing a mixture according to claim 1, comprising:

a) oxidative coupling according to reaction scheme A:

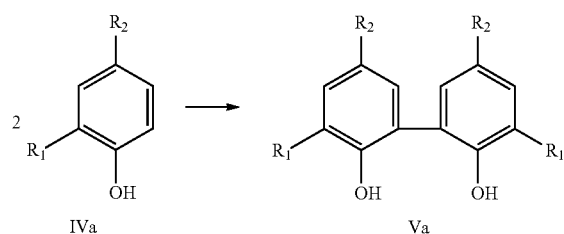

A b) oxidative coupling according to reaction scheme B:

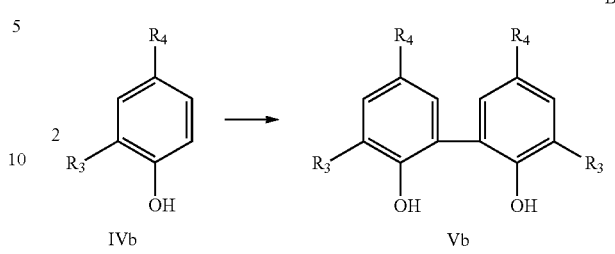

B c) reaction of the product from a) with PCl₃ according to reaction scheme C:

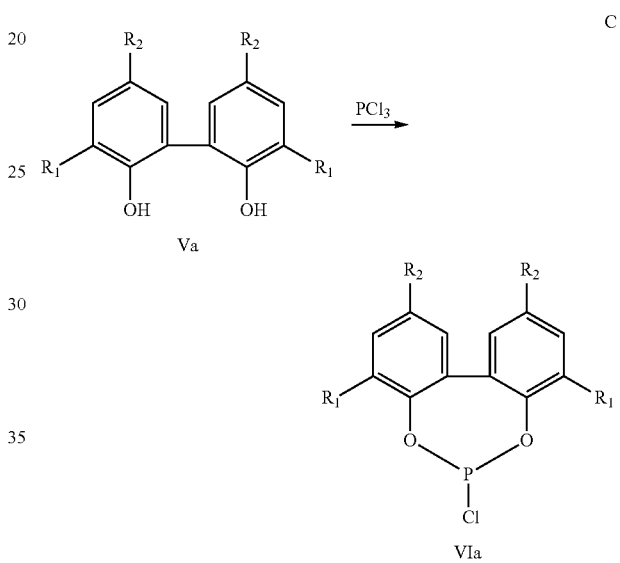

C d) reaction of the product from b) with the product from c) to give a mixture according to claim 1.

15. The process according to claim 14, further comprising:
e) reaction with M to give (Ib) and (IIb), where M is selected from the group consisting of Fe, Ru, Os, Co, Rh, Ir, Ni, Pd, and Pt.

16. A process for hydroformylating unsaturated compounds and mixtures thereof comprising contacting:
a composition according to claim 12, and
a gas mixture comprising carbon monoxide and hydrogen.

17. The process according to claim 16, wherein the unsaturated compounds and mixtures thereof are selected from the group consisting of:
hydrocarbon mixtures from steamcracking plants;
hydrocarbon mixtures from catalytically operated cracking plants;
hydrocarbon mixtures from oligomerization operations;
hydrocarbon mixtures comprising polyunsaturated compounds; and
unsaturated carboxylic acid derivatives.

18. The process according to claim 17, wherein the hydrocarbon mixtures include unsaturated compounds having 2 to 30 carbon atoms.

19. A catalyst in a hydroformylation reaction of unsaturated compounds and mixtures thereof that comprises the mixture according to claim 1.

* * * * *